US007919079B2

(12) United States Patent
Simmons et al.

(10) Patent No.: US 7,919,079 B2
(45) Date of Patent: Apr. 5, 2011

(54) CANCER IMMUNOTHERAPY COMPOSITIONS AND METHODS OF USE

(75) Inventors: Andrew Simmons, San Mateo, CA (US); Karin Jooss, Bellevue, WA (US); James Allison, New York, NY (US)

(73) Assignees: BioSante Pharmaceuticals, Inc., Lincolnshire, IL (US); The Regents of the University of California, Oakland, CA (US)

( * ) Notice: Subject to any disclaimer, the term of this patent is extended or adjusted under 35 U.S.C. 154(b) by 284 days.

(21) Appl. No.: 11/729,339

(22) Filed: Mar. 28, 2007

(65) Prior Publication Data
US 2008/0014222 A1 Jan. 17, 2008

Related U.S. Application Data

(60) Provisional application No. 60/788,296, filed on Mar. 31, 2006.

(51) Int. Cl.
*A01N 63/00* (2006.01)
(52) U.S. Cl. .................................. 424/93.21; 424/277.1
(58) Field of Classification Search .................. None
See application file for complete search history.

(56) References Cited

U.S. PATENT DOCUMENTS

| | | | |
|---|---|---|---|
| 5,078,996 A | 1/1992 | Conlon, III et al. | |
| 5,098,702 A | 3/1992 | Zimmerman et al. | |
| 5,436,146 A | 7/1995 | Shenk et al. | |
| 5,543,328 A | 8/1996 | McClelland et al. | |
| 5,637,483 A | 6/1997 | Dranoff et al. | |
| 5,686,279 A | 11/1997 | Finer et al. | |
| 5,731,190 A | 3/1998 | Wickham et al. | |
| 5,753,500 A | 5/1998 | Shenk et al. | |
| 5,756,086 A | 5/1998 | McClelland et al. | |
| 5,770,442 A | 6/1998 | Wickham et al. | |
| 5,846,767 A | 12/1998 | Halpin et al. | |
| 5,846,782 A | 12/1998 | Wickham et al. | |
| 5,904,920 A | 5/1999 | Dranoff et al. | |
| 5,922,315 A | 7/1999 | Roy | |
| 5,985,290 A | 11/1999 | Jaffee et al. | |
| 6,033,674 A | 3/2000 | Jaffee et al. | |
| 6,040,183 A | 3/2000 | Ferrari et al. | |
| 6,057,155 A | 5/2000 | Wickham et al. | |
| 6,093,570 A | 7/2000 | Ferrari et al. | |
| 6,117,425 A | 9/2000 | MacPhee et al. | |
| 6,127,525 A | 10/2000 | Crystal et al. | |
| 6,187,306 B1 | 2/2001 | Pardoll et al. | |
| 6,331,415 B1 | 12/2001 | Cabilly et al. | |
| 6,350,445 B1 | 2/2002 | Jaffee et al. | |
| 6,464,973 B1 | 10/2002 | Levitsky et al. | |
| 6,548,286 B1 | 4/2003 | Samulski et al. | |
| 6,555,368 B1 | 4/2003 | Curiel | |
| 6,602,503 B1 | 8/2003 | Lobb et al. | |
| 6,623,940 B1 | 9/2003 | Ledbetter et al. | |
| 6,683,170 B2 | 1/2004 | Curiel et al. | |
| 6,692,736 B2 | 2/2004 | Yu et al. | |
| 6,984,720 B1 * | 1/2006 | Korman et al. | 530/388.22 |
| 2002/0168342 A1 | 11/2002 | Wang et al. | |
| 2004/0265955 A1 * | 12/2004 | Fang et al. | 435/69.1 |
| 2005/0002916 A1 * | 1/2005 | Jooss et al. | 424/93.21 |

FOREIGN PATENT DOCUMENTS

| | | |
|---|---|---|
| WO | WO 99/39734 | 8/1999 |
| WO | WO 00/67576 | 11/2000 |
| WO | WO 00/72686 | 12/2000 |
| WO | WO 03/066810 | 12/2003 |
| WO | WO 2004/113493 | 12/2004 |
| WO | WO 2005/017149 | 2/2005 |

OTHER PUBLICATIONS

Elsas et al, J Exp Med, 1999, 190:355-366.*
Shi et al, Cancer Gene Therapy, 1999, 6:81-88.*
Griffin et al, J Immunol Methods, 2001, 248:77-90.*
Zheng et al, PNAS, 1998, 95:6284-6289.*
Allison, J,P., "Blockade of T Cell Inhibitory Signals: A New Paradigm in Tumor Immunotherapy?" Cancer Immunity, 5:9 (2005).
Altschul et al., "Basic Local Alignment Search Tool" J. Mol. Biol. 215:403-410 (1990).
Aoki et al., "Expression of Murine Interleukin 7 in a Murine Glioma Cell Line Results in Reduced Tumorigenicity in Vivo" PNAS 89(9):3850-3854 (1992).
Armstong et al., "Cytokine Modified Tumor Vaccines" Surgical Oncology Clin, N. AM. 11(3):681-696 (2002).
Batzer et al., "Enhanced Evolutionary PCR Using Oligonucleotides with Inosine at the 3'-Terminus" Nucleic Acid Res. 19(18): 5081 (1991).
Bett et al., "Packaging Capacity and Stability of Human Adenovius Type 5 Vectors" J. Virology 67:5911-5921 (1993).
Bodey et al., "Failure of Cancer Vaccines: The Significant Limitations of this Approach to Immunotherapy" 20:(4) 2665-2676 (2000).
Bossis and Chiorini, "Cloning of an Avian Adeno-Associated Virus (AAAV) and Generation of Recombinant AAAV Particles" J. Virol. 77(12):6799-6810 (2003).
Brunner et al., "CTLA-4-Mediated Inhibition of Early Events of T Cell Proliferation1" J. Immunology 162:5813-5820 (1999).
Chambers et al., "CTLA-4-Mediated Inhibition in Regulation of T Cell Responses: Mechanisms and Manipulation in Tumor Immunotherapy" Annual Rev. Immunol. 19:565-594 (2001).
Chang et al., "Immunogenetic Therapy of Human Melanoma Utlizing Autologous Tumor Cells Transduced to Secrete Granulocyte-Macrophage Colony-Stimulating Factor" Human Gene Therapy 11:839-850 (2000).
Chaplin et al., "Production of Interleukin-12 as a Self-Processing 2A Polypeptide" J. Interferon Cytokine Res. 19:235-241 (1999.

(Continued)

*Primary Examiner* — Misook Yu
*Assistant Examiner* — Mark Halvorson
(74) *Attorney, Agent, or Firm* — Ropes & Gray LLP; James F. Haley, Jr.

(57) ABSTRACT

Cellular compositions and methods for inducing an immune response to tumor cells are described. The cellular compositions include a tumor antigen and cells that have been modified to express a cytokine and one or more of a tumor antigen, anti-CTLA4 antibody and an additional cytokine. The cellular compositions find utility in methods for treating cancer.

28 Claims, 7 Drawing Sheets

OTHER PUBLICATIONS

Chu and Sharp, "SV40 DNA Transfection of Cells in Suspension: Analysis of the Efficiency of Transcription and Translation of T-antigen" Gene 13:197-202 (1981).

Darrow et al., "The Role of HLA Class I Antigens in Recognition of Melanoma Cells by Tumor-Specific Cytotoxic T Lymphocytes" J. Immunology 142:3329-3335 (1989).

de Felipe et al., Use of the 2A Sequence from Foot-and-Mouth Disease Virus in the Generation of Retroviral Vectors for Gene Therapy Gene Therapy 6:198-208 (1999).

de Felipe and Izquierdo, "Tricistronic and Tetracistronic Retroviral Vectors for Gene Transfer" Human Gene Therapy 11:1921-1931 (2000).

Donnelly et al., Analysis of the Aphthovirus 2A/2B Polyprotein 'Cleavage' Mechanism Indicates Not a Proteolytic Reaction, but a Novel Translational Effect: a Putative Ribosomal 'Skip' J. Gen. Virol. 82: 1013-1025 (2001).

Donnelly et al., "The Cleavage Activities of Foot and Mouth Disease Virus 2A Site-Directed Mutants and Naturally Occurring '2A-Like' Sequences" J. Gen. Virol. 82: 1027-1041 (2001).

Dranoff et al., "Vaccination with Irradiated Tumor Cells Engineered to Secrete Murine Granulocyte-Macrophage Colony-Stimulating Factor Stimulates Potent, Specific, and Long-Lasting Anti-Tumor Immunity" PNAS USA 90:3539-3543(1993).

Dull et al., "A Third-Generation Lentivirus Vector with a Conditional Packaging System" J. Virol. 72: 8463-8471 (1998).

Dummer, R., "GVAX Cell Genesys" Curr. Opinion Investig. Drugs 2(6):844-848 (2001).

Emens et al., "Clinical Protocol" Human Gene Therapy 15:313-337 (2004).

Fearon et al., "Interleukin-2 Production by Tumor Cells Bypasses T Helper Function in the Generation of an Antitumor Response" Cell 60:397-403 (1990).

Fields Virology Third Edition, edited by B.N. Fields et al., Lippincott Raven Publisher (1996), Chapter 58, "Retrovirdae: The Viruses and Their Relication", Classification, pp. 1768-1771, including Table 1.

Finer et al., "*kat:* A High-Efficiency Retroviral Transduction System for Primary Human T Lymphocytes," Blood, 83:43-50 (1994).

Gansbacher et al., "Retroviral Vector-Mediated γ-Interferon Gene Transfer into Tumor Cells Generates Potent and Long Lasting Antitumor Immunity," Cancer Research 50:7820-7825 (1990.

Gansbacher et al., "Interleukin 2 Gene Transfer Into Tumor Cells Abrogates Tumorigenicity and Induces Protective Immunity" J. Exp. Med. 172:1217-1224 (1990).

Gao et al., "Adeno-associated viruses undergo substantial evolution in primates during natural infections," PNAS USA 100:6081-6086 (2003).

Gao et al.,"Novel adeno-associated viruses from rhesus monkeys as vectors for human gene therapy," PNAS USA 99:11854-11859 (2002).

Golumbeck et al., "Treatment of Established Renal Cancer of Tumor Cells Engineer to Secrete Interleukin-4," Reports, 713-716 (1991).

Graham et al., "A new technique for the assay of infectivity of humans adenovirus 5," Virology 52:456-467 (1973).

Halpin et al., "Self-processing 2A-polyproteins—a system for coordinate expression of multiple proteins in transgenic plants," The Plant Journal 17:453-459 (1999.

Hartley and Rowe, "Naturally occurring murine leukemia viruses in wild mice: characterization of a new 'amphotropic' class," J. Virol. 19:19-25 (1976).

Hock et al., "Interleukin 7 induces CD4+ T cell-dependent tumor rejection," J. Exp. Med. 174:1291-1298 (1991).

Hom et al., "Common Expression of Melanoma Tumor-Associated Antigens Recognized by Human Tumor Infiltrating Lymphocytes: Analysis by Human Lymphocytes Antigen Restriction," Immunother. 10:153-164 (1991).

Huang et al., "Role of bone marrow derived cells in presenting MHC class I restricted tumour antigens," Science 264:961-965 (1994).

Huez et al., "Two Independent Internal Ribosome Entry Sites Are Involved in Translation Initiation of Vascular Endothelial Growth Factor mRNA," Mol. Cell. Biology 18(11): 6178-6190 (1998.

Jackson, R.J. and Kaminski, A., "Internal initiation of translation in eukaryotes: the picornavirus paradigm and beyond," RNA 1(10):985-1000 (1995.

Jackson, et al., "The Novel Mechanism of Initation of Picornavirus RNA Translation," Trends Biochem Sci. 15(12):477-483 (1990).

Jaffee et al., "Clinical Protocol, A Phase I Clinical Trial of Lethally Irradiated Allogeneic Pancreatic Tumor Cells Transfected with the GM-CSF Gene for the Treatment of Pancreatic Adenorcarcinoma," Human Gene Therapy, 9:1951-1971 (1998).

Jaffee et al., "Development and characterization of a cytokine-secreting pancreatic adenocarcinoma vaccine from primary tumors for use in clinical trials," Cancer J. Sci Am 4:194-203 (1998).

Jaffee et al., "Novel Allogeneic Granulocyte-Macrophage Colony-Stimulating Factor-Secreting Tumor Vaccine for Pancreatic Cancer: A Phase I Trial of Safety and Immune Activation," J. Clin. Oncol., 19:145:156 (2001).

Jaffee et al., "Gene therapy: its potential applications in the treatment of renal-cell carcinoma," Seminars in Oncology 22:81-91 (1995.

Kawakami et al., "Shared human melanoma antigens. Recognition by tumor infiltrating lymphocytes in HLA-A2.1 transfected melanomas," Journal of Immunology, 148:638-643 (1992).

Klein et al., "Properties of the K562 cell line, derived from a patient with chronic myeloid leukemia," Int. J. Cancer 18:421-431 (1976).

Kohler et al., "Derivation of specific antibody-producing tissue culture and tumor lines by cell fusion," Eur. J. Immunol. 6:511-519 (1976).

Korman et al., "Tumor immunotherapy: preclinical and clinical activity of anti-CTLA4 antibodies," Curr. Opin. Invest. Drugs 6:582-591 (2005).

Lee et al., "Genetic Immunotherapy of Established Tumors with Adenovirus-Murine Granulocyte-Macrophage Colony-Stimulating Factor," Human Gene Therapy, 8:187-193 (1997).

Lyerly, "Quantitating Cellular Immune Responses to Cancer Vaccines," Seminars in Oncology, 30(3):9-16 (2003.

McCarty et al., "Self-complementary recombinant adeno-associated virus (scAAV) vectors promote efficient transduction independently of DNA synthesis," Gene Therapy, 8:1248-1254 (2001).

Miller, "Human gene therapy comes of age," Nature, 357:455-460 (1992).

Miyazaki et al., "Expression vector system based on the chicken β-actin prmoter directs efficient production of interleukin-5," Gene, 79:269-277 (1989).

Mulligan et al., "Expression of a bacterial gene in mammalian cells," Science, 2099:1422-1427 (1980).

Nagai et al., "Irradiated Tumor Cells Adenovirally Engineered to Secrete Granulocyte/Macrophage-Colony-Stimulating Factor establish Antitumor Immunity and Eliminate Pre-existing Tumors in Syngeneic Mice," Cancer Immnunol. Immunother. 47:72-80 (1998).

Needleman, et al., "A general method applicable to the search for similarities in the amino acid sequence of two proteins," J. Mol. Biol. 48:443-453 (1970).

Nemunaitis et al., "Granulocyte-macrophage colony-stimulating factor gene-modified autologous tumor vaccines in non-small-cell lung cancer," Journal of the National Cancer Institute 96(4):326-331 (2004).

Oettgen et al., "The history of cancer immunotherapy," Biologic Therapy of Cancer, Chapter 6:87-119 (1991).

Ohtsuka et al., "An alternative approach to deoxyoligonucleotides as hybridization probes by insertion of deoxyinosine at ambiguous codon positions," The Journal of Biological Chemistry 260:2605-2608 (1985).

Ory, et al., "A stable human-derived packaging cell line for production of high titer retrovirus/vesicular stomatitis virus G pseudotypes," Proc. Natl. Acad. Sci. 93:11400-11406 (1996).

Palmenberg, "Proteolytic processing of picornaviral polyprotein," Annu. Ref. Microbiol. 44:603-623 (1990).

Pearson & Lipman, "Improved tools for biological sequence comparision," PNAS USA 85:2444-2448 (1988).

Phan et al., "Blockade of CTLA-4 with MDX-010 in humans can induce both autoimmunity and cancer regression," Proc. Am. Soc. Clin. Oncol., 22:852, Abstract 3424 (2003).

Porgador et al., "Immunotherapy of tumor metastasis via gene therapy," Nat. Immun., 13:113-130 (1994).

Roosien et al., "Synthesis of foot-and-mouth disease virus capsid proteins in insect cells using baculovirus expression vectors," *Journal of General Virology* 71:1703-1711 (1990).

Rossolini et al., "Use of deoxyinosine-containing primers vs degenerate primers for polymerase chain reaction based on ambiguous sequence information," *Molecular and Cellular Probes* 8:91-98 (1994).

Ryan et al., "Foot-and-mouth disease virus 2A oligopeptide mediated cleavage of an artificial polyprotein," *EMBO J.* 13:928-933 (1994).

Ryan et al., "Cleavage of foot-and-mouth disease virus polyprotein is mediated by residues located within a 19 amino acid sequence," *Journal of General Virology* 72:2727-2732 (1991).

Ryan et al., "Specificity of enzyme-substrate interactions in foot-and-mouth disease virus polyprotein processing," *Virology* 173:35-45 (1989).

Salgia et al., "Vaccination with irradiated autologous tumor cells engineered to secrete granulocyte-macrophage colony-stimulating factor augments antitumor immunity in some patients with metastatic non-small-cell lung carcinoma," *J. Clin. Oncol.*, 21(4):624-630 (2003).

Sanderson et al., "Autoimmunity in a phase I trial of a fully human anti-cytoxic t-lymphocyte antigen-4 monoclonal antibody with multiple melanoma peptides and montanide ISA 51 for patients with resected stages III and IV melanoma," *J. Clin. Oncol.* 23:741-750 (2005).

Simons et al., "Bioactivity of autologous irradiated renal cell carcinoma vaccines generated by ex vivo granulocyte-macrophage colony-stimulating factor gene transfer," *Cancer Research* 57:1537-1546 (1997).

Simons et al., "Induction of immunity to prostrate cancer antigens: results of a clinical trial of vaccination with irradiated autologous prostrate tumor cells engineered to secrete granulocyte-macrophage colony-stimulating factor using ex vivo gene transfer," *Cancer Research* 59:5160-5168 (1999).

Smith et al., "Comparison of biosequences," *Advances in Applied Mathematics* 2:482-489 (1981).

Soiffer et al., "Vaccination with irradiated autologous melanoma cells engineered to secrete human granulocyte-macrophage colony-stimulating factor generates potent antitumor immunity in patients with metastatic melanoma," *Proc. Natl. Acad. Sci. USA* 95:13141-13146 (1998).

Soiffer et al., "Vaccination with irradiated, autologous melanoma cells engineered to secrete granulocyte-macrophage colony-stimulating factor by adenoviral-mediated gene transfer augments antitumor immunity in patients with metastatic melanoma," *J. Clin. Oncol.* 21(17):3343-3350 (2003).

Southern et al., "Transformation of mammalian cells to antibiotic resistance with a bacterial gene under control of the SV40 early region promoter," *Journal of Molecular and Applied Genetics*, "Transformation of mammalian cells to antibiotic resistance with a bacterial gene under control of the SV40 early region promoter," *Journal of Molecular and Applied Genetics* 1:327-341 (1982).

Sugden et al., "A vector that replicates as a plasmid and can be efficiently selected in B-lymphoblasts transformed by Epstein-Barr virus," *Molecular and Cellular Biology* 5(2):410-413 (1985).

Szymczak et al., "Correction of multi-gene deficiency in vivo using a single 'self-cleaving' 2A peptide-based retroviral vector," *Nature Biotechnology* (Letters) 22(5):589-594 (2004).

Teng, et al., "Long-term inhibition of tumor growth by tumor necrosis factor in the absence of cachexia or t-cell immunity," *Proc. Natl. Acad. Sci. USA* 88:3535-3539 (1991).

Zennou et al., "HIV-1 genome nuclear import is mediated by a central DNA flap," *Cell* 101:173-185 (2000).

Zufferey, et al., "Self-inactivating lentivirus vector for safe and efficient in vivo gene delivery," *Journal of Virology* 72(12):9873-9880 (1998).

Simmons et al, "Local secretion of anit-CTLA4 antibody from a GM-CSF-secreting tumor cell vaccine enhances vaccine efficacy," Proceedings of the American Association for Cancer Research Annual Meeting, 47:359 (2006) (Abstract Only).

Akiyama et al., "Enhancement of antitumor immunity against B16 melaneoma tumor using genetically modified dendritic cells to produce cytokines," Gene Therapy, 7:2113-2121 (2000).

Hodi et al., "Biologic activity of cytotoxic T lymphocyte-associated antigen 4 antibody blockade in previously vaccinated metastatic melanoma and ovarian carcinoma patients," PNAS, 100:4712-4717 (2003).

Ribas et al., "Genetically modified dendritic cells for caner immunotherapy," Current Gene Therapy, 5:619-628 (2005).

* cited by examiner

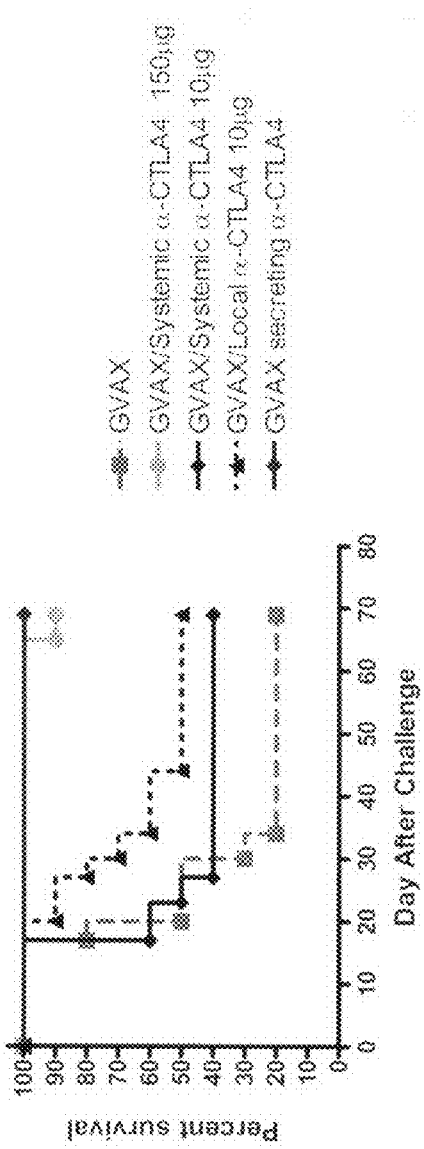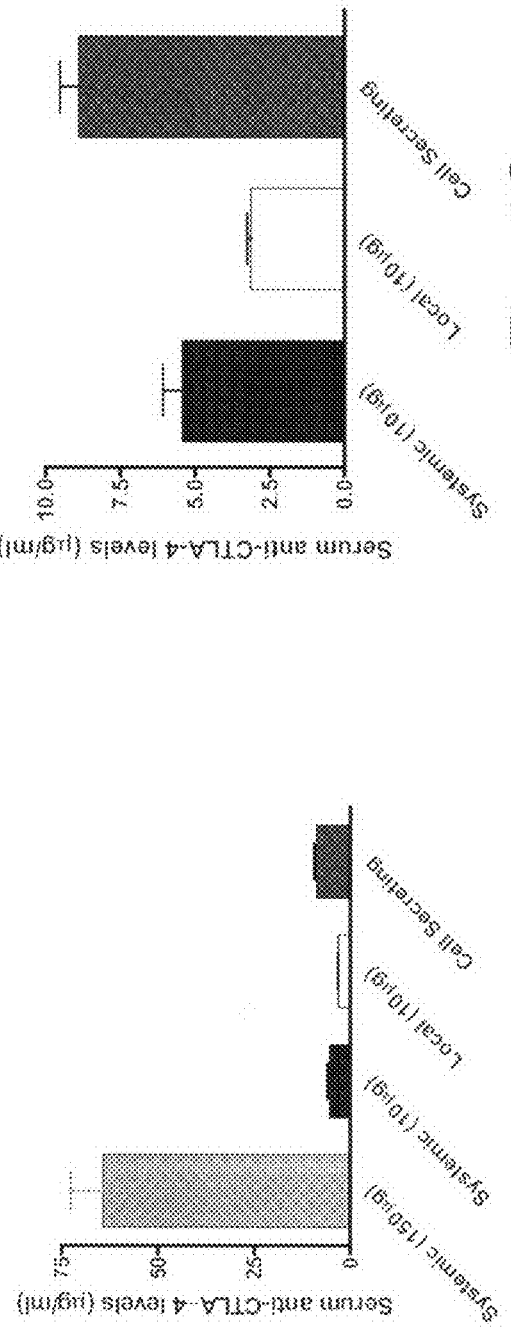
Fig. 4A
Fig. 4B
Fig. 4C

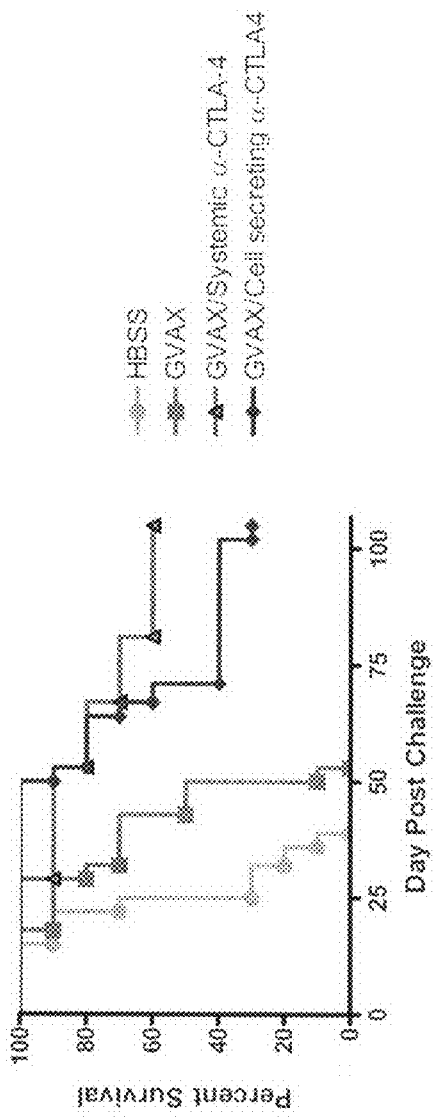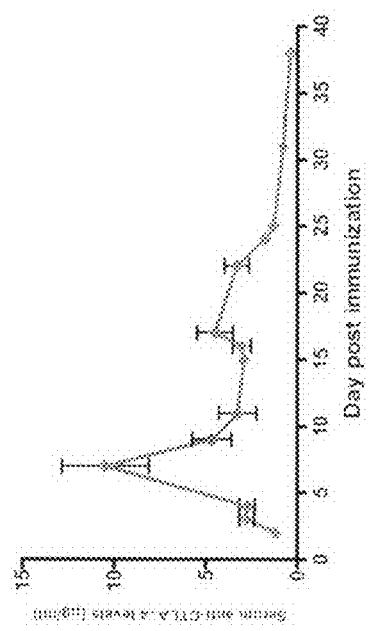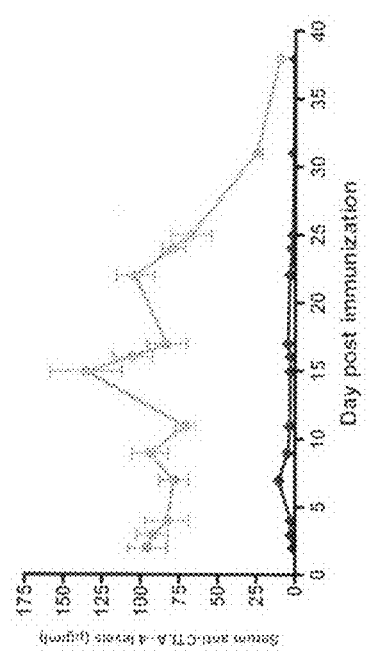
Fig. 5A
Fig. 5B
Fig. 5C

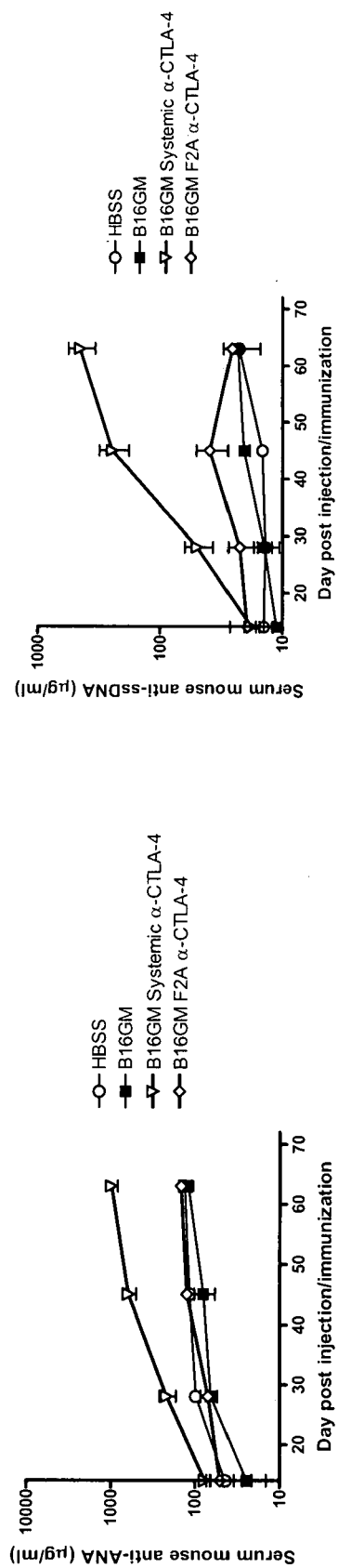
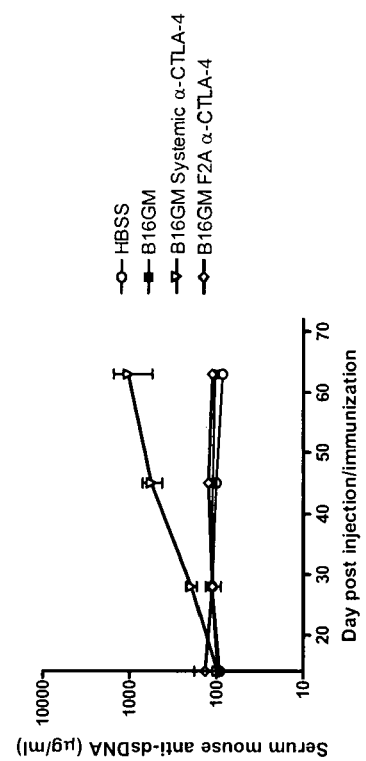
Fig. 7A
Fig. 7B
Fig. 7C ously (e.g.# CANCER IMMUNOTHERAPY COMPOSITIONS AND METHODS OF USE

CROSS-REFERENCE TO RELATED APPLICATIONS

This application claims the priority benefit of U.S. Provisional Patent Application No. 60/788,296, filed Mar. 31, 2006. The priority application is expressly incorporated by reference herein in its entirety.

The Sequence Listing for this application is submitted as a text file via EFS-Web, and is incorporated by reference herein. The name of the text file containing the Sequence Listing is sequence.txt. The text file is 5473 bytes (5.34 KB), and was created on Aug. 17, 2009.

BACKGROUND OF THE INVENTION

1. Field of the Invention

The present invention relates to cellular compositions and methods for inducing an immune response to tumor cells. The cellular compositions comprise cells that have been genetically modified to express an anti-cytotoxic T lymphocyte-associated antigen-4 (CTLA-4) antibody and a cytokine, whereby the local, sustained cell-based expression of the anti-CTLA4 antibody at the immunization site significantly reduces the therapeutic concentration compared to systemic administration.

2. Background of the Technology

One therapeutic approach to cancer is the use of autologous or allogeneic cancer cells as vaccines to augment anti-tumor immunity (Oettgen et al., The History of Cancer Immunotherapy, In: Biologic Therapy of Cancer, Devita et al. (eds.) J. Lippincot Co., pp 87-199, 1991; Armstrong T D and Jaffee E M, Surg Oncol Clin N Am. 11(3):681-96, 2002 and Bodey B et al., Anticancer Res 20(4):2665-76, 2000). An expansion of this approach involves the use of genetically modified tumor cells that express cytokines locally at the immunotherapy site.

Numerous cytokines have been shown to play a role in regulation of the immune response to tumors. For example, U.S. Pat. No. 5,098,702 describes use of combinations of TNF, IL-2 and IFN-beta in synergistically effective amounts to combat existing tumors. U.S. Pat. Nos. 5,078,996, 5,637,483, 5,904,920 and 6,350,445 describe the use of GM-CSF for treatment of tumors. Activity has been demonstrated in tumor models using a variety of immunomodulatory cytokines, including IL-4, IL-2, TNF alpha, G-CSF, IL-7, IL-6 and GM-CSF, as described in Golumbeck P T et al., Science 254:13-716, 1991; Gansbacher B et al., J. Exp. Med. 172: 1217-1224, 1990; Fearon E R et al., Cell 60:397-403, 1990; Gansbacher B et al., Cancer Res. 50:7820-25, 1990; Teng M et al., PNAS 88:3535-3539, 1991; Columbo M P et al., J. Exp. Med. 174:1291-1298, 1991; Aoki et al., Proc Natl Acad Sci USA. 89(9):3850-4, 1992; Porgador A, et al., Nat Immun. 13(2-3):113-30, 1994; Dranoff G et al., PNAS 90:3539-3543, 1993; Lee C T et al., Human Gene Therapy 8:187-193, 1997; Nagai E et al., Cancer Immunol. Immonther. 47:2-80, 1998 and Chang A et al., Human Gene Therapy 11:839-850, 2000, respectively. Clinical trials employing GM-CSF-expressing autologous or allogeneic cellular vaccines (GVAX®) have commenced for treatment of prostate cancer, melanoma, lung cancer, pancreatic cancer, renal cancer, and multiple myeloma (Dummer R., Curr Opin Investig Drugs 2(6):844-8, 2001; Simons J et al., Cancer Res. 15; 59(20):5160-8, 1999; Soiffer R et al., PNAS 95:13141-13146, 1998; Simons J et al., Cancer Res. 15; 57:1537-1546, 1997; Jaffee E et al., J. Clin Oncol. 19:145-156, 2001; and Salgia R et al., J. Clin Oncol. 21:624-630, 2003; Soiffer et al. J Clin Oncol 2003 21:3343B50; Nemunaitis et al. J Natl Cancer Inst. Feb. 18, 2004 96(4):326-31).

GM-CSF-expressing autologous or allogeneic cellular cancer immunotherapies have been described previously (e.g. see U.S. Pat. Nos. 6,464,973, 6,350,445, 6,187,306, 6,033,674, 5,985,290 and 5,637,483). However, there remains a need for improved GVAX®-based immunotherapy strategies for treatment of cancer.

Cytotoxic T lymphocyte-associated antigen 4 (CTLA-4; CD152) is an immunosuppressive molecule expressed on activated T cells and a subset of CD4+CD25+ T cells. CTLA-4 is a well-known regulator of T cell activation (Chambers, C. A. et al., Annu. Rev. Immunol. 19:565, 2001). CTLA-4 signaling has been shown to inhibit events early in T cell activation both at the level of IL-2 transcription and at the level of IL-2-independent events of the cell cycle (Brunner et al., J. Immunol., 1999, 162: 5813-5820).

CTLA-4, which binds B7-1/2 is essential for down-regulation of T-cell responses. ctla-4$^{-/-}$ mice have been observed to suffer from a lethal lymphoproliferative response that is initiated by uncontrolled T-cell expansion. Thus, CD28 and CTLA-4 play critical roles in regulating early stages of the T-cell response. CTLA-4 has also been shown to regulate both the occurrence and severity of experimental autoimmune disease in mice (Allison, J. P., Cancer Immunity, Vol. 5 Suppl. 1, p. 9; 6 Apr. 2005).

A fully human monoclonal antibody to human CTLA-4 has shown anti-tumor activity in Phase I/II and II trials (Medarex). In a phase I study that involved administration of a fully human CTLA-4-blocking monoclonal antibody (MDX-010) combined with melanoma peptide vaccines, eight out of nineteen patients with resected stage III or IV metastatic melanoma who received repeat doses of MDX-010 developed significant autoimmune toxicities. The symptoms included uveitis, rashes, and gastrointestinal reactions (diarrhea and abdominal pain). See, e.g., Sanderson K. et al., J Clin Oncol 23:741-750, 2005.

In another study, fourteen patients with metastatic melanoma received intravenous administration of a fully human anti-CTLA-4 antibody (MDX-010) at 3 mg/kg every 3 weeks as tolerated in conjunction with subcutaneous vaccination with two modified HLA-A 0201-restricted gp100 peptides. The results indicated that while three patients had objective cancer regression, six patients (43%) developed autoimmune events including three patients with dermatitis, two with colitis/enterocolitis and one with hepatitis, all of which were self-limited or responsive to systemic steroids. (G. Q. Phan et al., Proc Am Soc Clin Oncol 22: page 852, 2003, Abstr 3424). These data suggest that CTLA-4 may have a therapeutic benefit, however, systemic administration of anti-CTLA4 antibody sufficient to achieve to efficacy in a clinical setting may have related toxicity. Therefore, there is a need to develop compositions that overcome the potential toxicity by allowing for a lower systemic level of anti-CTLA4 antibody which is also efficacious.

SUMMARY OF THE INVENTION

The invention provides cellular immunotherapy compositions for generating an immune response to cancer in a human subject, wherein the cell based immunotherapy compositions include a tumor antigen and one or more populations of cells genetically modified to express an anti-cytotoxic T lymphocyte-associated antigen-4 (CTLA-4) antibody and a cytokine, e.g., GM-CSF and methods of using the same for treatment of cancer in a patient. Following administration of the cell based immunotherapy composition to a human subject, an immune response to the tumor antigen is detected wherein the immune response is not detected in the human subject prior to administering the cellular composition.

In one aspect, the tumor antigen is expressed by a cell and the cell is genetically modified.

The same or a different populations of cells may be genetically modified to express the coding sequence for a cytokine or an anti-CTLA4 antibody.

In one aspect, a tumor antigen-expressing population of cells is genetically modified to express the coding sequence for both a cytokine and an anti-CTLA4 antibody.

The genetically modified cells may be autologous, allogeneic or bystander cells and may or may not express a tumor antigen.

In one embodiment, an autologous, allogeneic or bystander tumor antigen-expressing population of cells is genetically modified to express the coding sequence for a cytokine, such as GM-CSF.

In another embodiment, an autologous, allogeneic or bystander tumor antigen-expressing population of cells is genetically modified to express the coding sequence for a cytokine, such as GM-CSF, and an anti-CTLA4 antibody.

In yet another embodiment, an autologous, allogeneic or bystander tumor antigen-expressing population of cells is genetically modified to express the coding sequence for an anti-CTLA4 antibody.

BRIEF DESCRIPTION OF THE FIGURES

FIG. 4A shows a Kaplan-Meier graph of the results of a study in a BALB/c mouse CT26 tumor model demonstrating that retroviral transduced cytokine-expressing cancer immunotherapy expressing the anti-CTLA4 antibody improves survival of tumor bearing animals at lower systemic antibody concentrations. On Day 0, BALB/c mice were inoculated subcutaneously with 5×10$^5$ live CT26 tumor cells. Three days later, mice were immunized with 1×10$^6$ irradiated GM-CSF secreting CT-26, or with the same number of irradiated CT-26 cells secreting both GM-CSF and anti-CTLA4 antibody. Control groups were immunized on Day 3 with 1×10$^6$ irradiated GM-CSF secreting CT-26 tumor cells, and systemic (intraperitoneal—150 ug, 10 ug) or local (mixed with cytokine-expressing cancer immunotherapy—10 ug SC) administration of recombinant anti-CTLA4 antibody. Mice were subjected to repeated immunizations and antibody injections on Days 13 and 27. Mice were monitored for the formation of palpable tumors twice weekly, and sacrificed if tumors became necrotic or exceeded 1500 mm$^3$ in size.

FIGS. 4B and 4C show the concentration of anti-CTLA4 antibody present in serum from animals collected at Day 3 post antibody administration in FIG. 4A.

FIG. 5A shows a Kaplan-Meier graph illustrating that local expression of an anti-CTLA4 antibody from retroviral transduced, cytokine-expressing tumor cells improved survival of tumor bearing animals in the B16F10 melanoma model. On Day 0, C57BL/6 mice were challenged with 2×10$^5$ live B16F10 tumor cells. Mice were immunized on Day 1 with 3×10$^6$ irradiated GM-CSF secreting B16F10 tumor cells, or with the same number of irradiated B16F10 cells secreting both GM-CSF and anti-CTLA4 antibody. A separate group was immunized with irradiated GM-CSF secreting tumor cells, and systemic (intraperitoneal) administration of recombinant antibody on Days 2 (150 ug) and 5 (100 ug). A second round of immunizations and antibody injections was administered starting on day 14. Tumor burden was monitored and mice were sacrificed when challenge tumors reached 1500 mm$^3$ or severe ulceration developed.

FIGS. 5B and 5C show the concentration of anti-CTLA4 antibody present in serum from animals collected at specified days post systemic or locally-expressed antibody administration in FIG. 5A.

FIG. 6A) or 5×10$^3$ irradiated B16F10 cells (FIG. 6b). Positive spots were enumerated using an automated plate scanning service.

FIGS. 7A-C show of the results of a study in C57Bl/6 mice demonstrating that administration of a cytokine-expressing cancer immunotherapy that also locally expresses F2A anti-CTLA antibody results in long-term, sustainable, in vivo expression of anti-CTLA4 antibody. On Day 0, mice were inoculated subcutaneously (SC) with 2×10$^5$ live B16F10 tumor cells. On Day 1, mice were divided into 4 separate groups: one set each received a single intraperitoneal (ip)

Figure 1:
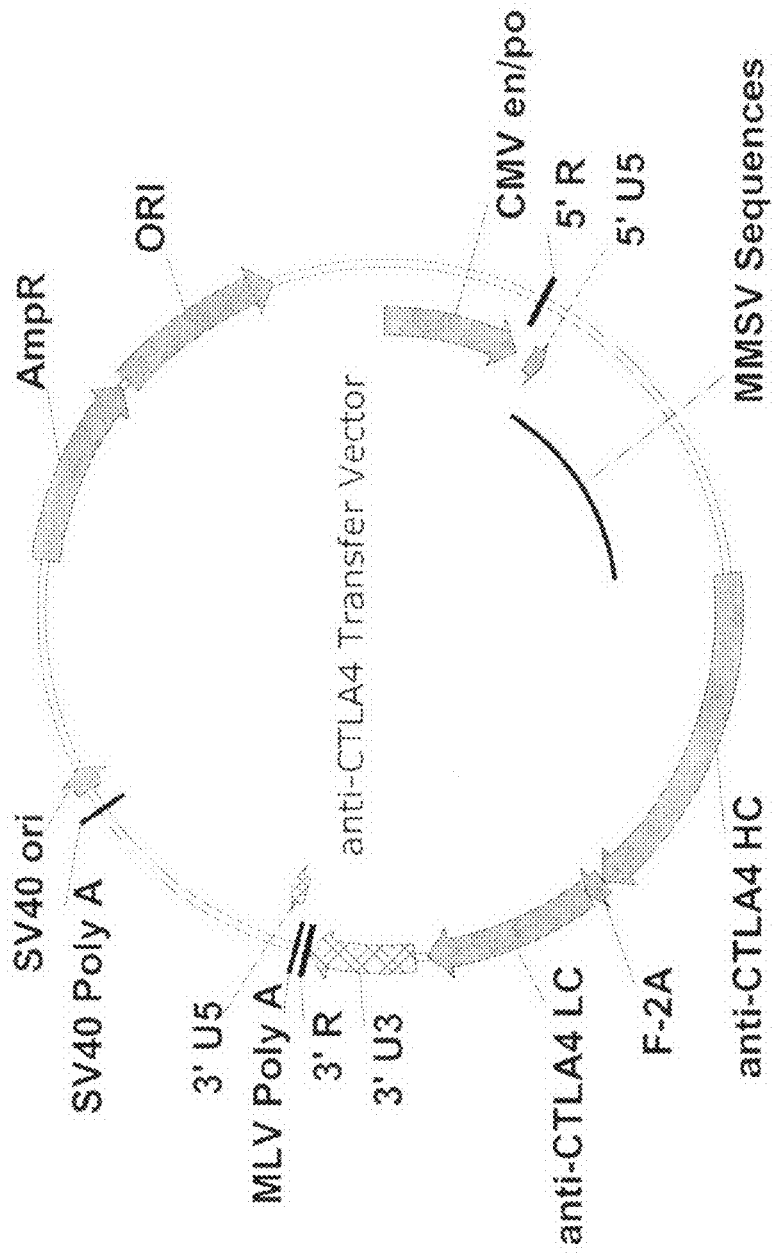
FIG. 1 depicts a retroviral vector designated as an anti-CTLA4 transfer vector, the construction of which is described in Example 1.
Figure 2B:
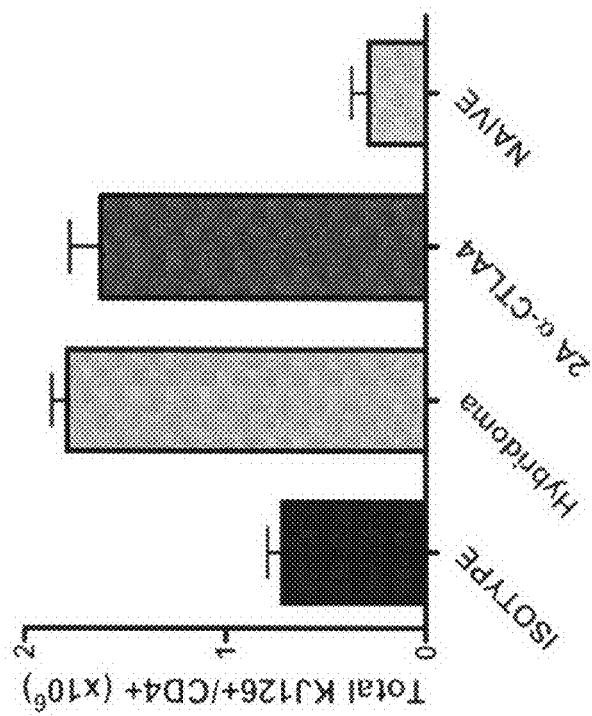
FIGS. 2A and 2B illustrate an outline of the study (FIG. 2A) and the results (FIG. 2B) demonstrating that anti-CTLA4 antibody expressed by a retroviral transduced cytokine-expressing cancer immunotherapy composition is functional and augments the expansion of adoptively transferred transgenic T cells upon immunization with purified ovalbumin. On day—2, 1-3×10$^6$ splenocytes from DO11.01 transgenic mice, which produce T cells specific for the OVA$_{323-339}$ peptide, were adoptively transferred into recipient Balb/c mice by iv administration. On day 0, mice were injected with 500 ug of the surrogate antigen, ovalbumin and subsequently administered subcutaneously (SC) dorsal 100 ug of: a control IgG2b control antibody (ISOTYPE); an anti-CTLA4 antibody purified from 9D9 expressing hydridoma (Hybridoma); an anti-CTLA4 antibody purified from retroviral transduced B16F10 expressing the anti-CTLA4 antibody (2A-anti-CTLA4); or vehicle (NAÏVE) with Days 0 and 1. On Day 4, mice were euthanized, the spleens and lymph nodes were harvested, and number of transgenic DO11.01 was determined using the DO11.01-specific monoclonal antibody KJ126. Shown is the absolute number of ovalbumin-specific CD8 T cells in spleen (FIG. 2B).
Figure 2A:
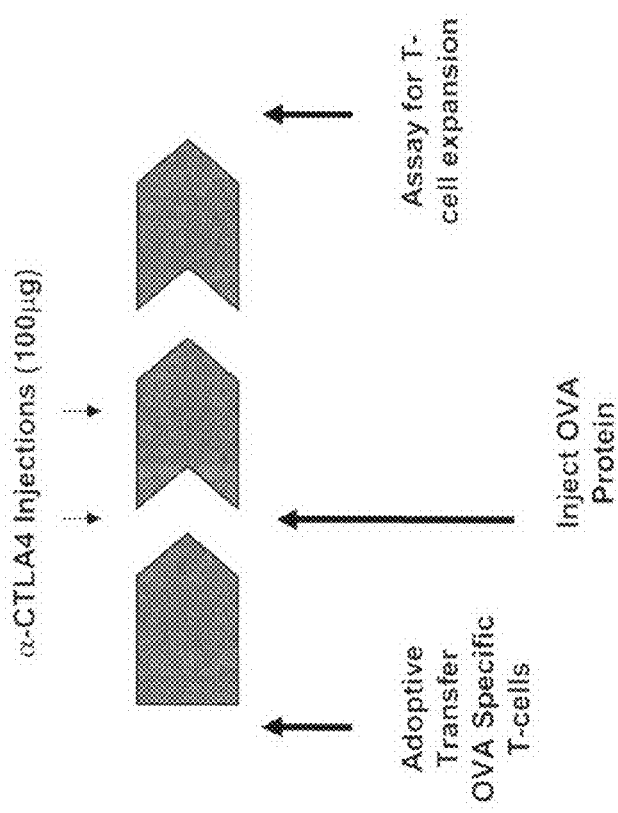

administration of HBSS (open circles); $3\times10^6$ irradiated B16F10 tumor cells engineered to express GM (B16GM; closed squares); $3\times10^6$ irradiated B16GM plus a systemic injection of CTLA4 (B16GM systemic α-CTLA4; open triangles); or $3\times10^6$ irradiated B16GM engineered to secrete anti-CTLA-4 using an F2A cassette (open diamonds). At the time points indicated serum was collected and evaluated for the levels of anti-nuclear (FIG. 7A), ss-DNA (FIG. 7B), and ds-DNA (FIG. 7C), antibodies by ELISA.

DETAILED DESCRIPTION OF THE INVENTION

Definitions

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, Molecular Cloning (Cold Spring Harbor Laboratory Press, Cold Spring Harbor, N.Y.); Sambrook et al., 1989, Molecular Cloning, 2nd Ed. (Cold Spring Harbor Laboratory Press, Cold Spring Harbor, N.Y.); Sambrook and Russell, 2001, Molecular Cloning, 3rd Ed. (Cold Spring Harbor Laboratory Press, Cold Spring Harbor, N.Y.); Ausubel et al., 1992, Current Protocols in Molecular Biology (John Wiley & Sons, including periodic updates); Glover, 1985, DNA Cloning (IRL Press, Oxford); Anand, 1992, Techniques for the Analysis of Complex Genomes, Academic Press, New York; Guthrie and Fink, 1991, Guide to Yeast Genetics and Molecular Biology, Academic Press, New York; Harlow and Lane, 1988, Antibodies, (Cold Spring Harbor Laboratory Press, Cold Spring Harbor, N.Y.); Jakoby and Pastan, 1979; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Riott, Essential Immunology, 6$^{th}$ Edition, Blackwell Scientific Publications, Oxford, 1988; Hogan et al., Manipulating the Mouse Embryo, (Cold Spring Harbor Laboratory Press, Cold Spring Harbor, N.Y., 1986).

Unless otherwise indicated, all terms used herein have the same meaning as they would to one skilled in the art and the practice of the present invention will employ, conventional techniques of microbiology and recombinant DNA technology, which are within the knowledge of those of skill of the art.

In describing the present invention, the following terms are employed and are intended to be defined as indicated below.

The term "nucleic acid" refers to deoxyribonucleotides or ribonucleotides and polymers thereof ("polynucleotides") in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid molecule/polynucleotide also implicitly encompasses conservatively modified variants thereof (e.g. degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260: 2605-2608 (1985); Rossolini et al., Mol. Cell. Probes 8: 91-98 (1994)). Nucleotides are indicated by their bases by the following standard abbreviations: adenine (A), cytosine (C), thymine (T), and guanine (G).

The terms "vector," "polynucleotide vector," "polynucleotide vector construct," "nucleic acid vector construct," and "vector construct" are used interchangeably herein to mean any nucleic acid construct for gene transfer, as understood by one skilled in the art.

In one approach, the vector is a viral vector. As used herein, the term "viral vector" is used according to its art-recognized meaning. It refers to a nucleic acid vector construct that includes at least one element of viral origin and may be packaged into a viral vector particle. The viral vector particles may be utilized for the purpose of transferring DNA, RNA or other nucleic acids into cells either in vitro or in vivo.

The terms "virus," "viral particle," "vector particle," "viral vector particle," and "virion" are used interchangeably and are to be understood broadly as meaning infectious viral particles that are formed when, e.g., a viral vector of the invention is transduced into an appropriate cell or cell line for the generation of infectious particles. Viral particles according to the invention may be utilized for the purpose of transferring DNA into cells either in vitro or in vivo. The vectors utilized in the present invention may optionally code for a selectable marker.

An "adenovirus vector" or "adenoviral vector" (used interchangeably) as referred to herein is a polynucleotide construct that can be packaged into an adenoviral virion. Exemplary adenoviral vectors of the invention include, but are not limited to, DNA, DNA encapsulated in an adenovirus coat, adenoviral DNA packaged in another viral or viral-like form (such as herpes simplex, and AAV), adenoviral DNA encapsulated in liposomes, adenoviral DNA complexed with polylysine, adenoviral DNA complexed with synthetic polycationic molecules, conjugated with transferrin, or complexed with compounds such as PEG to immunologically "mask" the antigenicity and/or increase half-life, or conjugated to a non-viral protein.

A "selectable marker" is a protein the expression of which in a cell gives the cell a selective advantage. The selective advantage possessed by cells transformed with the selectable marker gene may be due to their ability to grow in the presence of a negative selective agent, such as an antibiotic, compared to the growth of non-transduced cells. The selective advantage possessed by the transformed cells, compared to non-transduced cells, may also be due to their enhanced or novel capacity to utilize an added compound as a nutrient, growth factor or energy source. Selective marker proteins include those that allow detection of the transduced cells and possibly their separation from non-transduced cells. While any selectable marker can be used, selectable markers for use in such expression vectors are generally known in the art and the choice of the proper selectable marker will depend on the host cell and application. For example, Green Fluorescent Protein (GFP) can be used as a selectable marker. Examples of selectable marker genes which encode proteins that confer resistance to antibiotics or other toxins include ampicillin, methotrexate, tetracycline, neomycin (Southern et al., J., J Mol Appl Genet. 1982; 1(4):327 41 (1982)), mycophenolic acid (Mulligan et al., Science 209:1422 7 (1980)), puromycin, zeomycin, hygromycin (Sugden et al., Mol Cell Biol. 5(2):410 3 (1985)) or G418.

The term "transduction" refers to the delivery of a nucleic acid molecule into a recipient cell either in vivo or in vitro via infection, internalization, transfection or any other means. Transfection may be accomplished by a variety of means known in the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics, see Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. Gene 13:197, 1981. Such techniques can be used to introduce one or more exogenous DNA moieties, such as a plasmid vector and other nucleic acid molecules, into suitable host cells. The term refers to both stable and transient uptake of the genetic material.

The term "recombinant" as used herein with reference to nucleic acid molecules refers to a combination of nucleic acid molecules that are joined together using recombinant DNA technology into a progeny nucleic acid molecule. As used herein with reference to viruses, cells, and organisms, the terms "recombinant," "transformed," and "transgenic" refer to a host virus, cell, or organism into which a heterologous nucleic acid molecule has been introduced or a native nucleic acid sequence has been deleted or modified. In the case of introducing a heterologous nucleic acid molecule, the nucleic acid molecule can be stably integrated into the genome of the host or the nucleic acid molecule can also be present as an extrachromosomal molecule. Such an extrachromosomal molecule can be auto-replicating. Recombinant viruses, cells, and organisms are understood to encompass not only the end product of a transformation process, but also recombinant progeny thereof. A "non-transformed", "non-transgenic", or "non-recombinant" host refers to a wildtype virus, cell, or organism that does not contain the heterologous nucleic acid molecule.

"Regulatory elements" are sequences involved in controlling the expression of a nucleotide sequence. Regulatory elements include promoters, enhancers, and termination signals. They also typically encompass sequences required for proper translation of the nucleotide sequence.

The term "promoter" refers to an untranslated DNA sequence usually located upstream of the coding region that contains the binding site for RNA polymerase II and initiates transcription of the DNA. The promoter region may also include other elements that act as regulators of gene expression. The term "minimal promoter" refers to a promoter element, particularly a TATA element that is inactive or has greatly reduced promoter activity in the absence of upstream activation elements.

The term "enhancer" within the meaning of the invention may be any genetic element, e.g., a nucleotide sequence that increases transcription of a coding sequence operatively linked to a promoter to an extent greater than the transcription activation effected by the promoter itself when operatively linked to the coding sequence, i.e. it increases transcription from the promoter.

A nucleotide sequence is "operatively linked" or "operably linked" (used interchangeably) when it is placed into a functional relationship with another nucleotide sequence. For example, a promoter or regulatory DNA sequence is said to be "operatively linked" to a DNA sequence that codes for a RNA or a protein if the two sequences are situated such that the promoter or regulatory DNA sequence affects the expression level of the coding or structural DNA sequence. Operatively linked DNA sequences are typically, but not necessarily, contiguous.

The term "expression" refers to the transcription and/or translation of an endogenous gene, transgene or coding region in a cell. In the case of an antisense construct, expression may refer to the transcription of the antisense DNA only. The vectors of the invention contain a coding sequence for a protein or fragments thereof (e.g. anti-CTLA4 antibody, tumor antigen, GM-CSF). The coding sequences are operatively linked to a heterologous promoter that will be constitutively or inducibly active in the target cell, along with other control elements and a poly-A sequence necessary for transcription and translation of the protein. When engineering vectors for the expression of antigens, the expression vector may contain sequences that direct the cellular localization of the antigen. For example, antigen expression may be cytosolic; signal sequences for secretion may be employed, or sequences for stable association with the cell outer membrane. For the latter embodiment, a vector encodes an antigen and a transmembrane region in the same open reading frame, the transmembrane region being either upstream or downstream from the antigen coding region and optionally separated by an in-frame spacer region. The transmembrane region may be modeled on other known transmembrane proteins, or be an artificially designed polypeptide segment with a high degree of lipophilicity. In some embodiments, a combination of expression patterns may be used, either by the same cell or in distinct cell populations. The expression cassette thus composed is introduced into the cell by any method known in the art, such as calcium-phosphate precipitation, insertion using cationic liposomes, or by using a viral vector tropic for the cells.

The term "tumor selective promoter activity" as used herein means that the promoter activity of a promoter fragment is more active in tumor cells than in non-tumor cell types.

A "self-processing cleavage site" or "self-processing cleavage sequence" as referred to herein is a DNA or amino acid sequence, wherein upon translation, rapid intramolecular (cis) cleavage of a polypeptide comprising the self-processing cleavage site occurs to result in expression of discrete mature protein or polypeptide products. A self-processing cleavage site demonstrates a translational effect by modifying the activity of the ribosome to promote hydrolysis of an ester linkage, thereby releasing the polypeptide from the translational complex in a manner that allows the synthesis of a discrete downstream translation product to proceed (Donnelly et al. J Gen Virol. May 2001; 82(Pt 5):1013-25). Alternatively, a 2A site, sequence or domain demonstrates "autoproteolysis" or "cleavage" by cleaving its own C-terminus in cis to produce primary cleavage products (Furler; Palmenberg, Ann. Rev. Microbiol. 44:603-623 (1990)).

As used herein, the term "additional proteolytic cleavage site", refers to a sequence which is incorporated into an expression construct of the invention adjacent a self-processing cleavage site, such as a 2A or 2A like sequence, and provides a means to remove additional amino acids that remain following cleavage by the self processing cleavage sequence. Exemplary "additional proteolytic cleavage sites" are described herein and include, but are not limited to, furin cleavage sites with the consensus sequence RXK(R)R (SEQ ID NO: 10). Such furin cleavage sites can be cleaved by endogenous subtilisin-like proteases, such as furin and other serine proteases within the protein secretion pathway.

As used herein, the terms "immunoglobulin" and "antibody" may be used interchangeably and refer to intact immunoglobulin or antibody molecules as well as fragments thereof, such as Fa, F (ab')2, and Fv, which are capable of binding an antigenic determinant. Such an "immunoglobulin" and "antibody" is composed of two identical light polypeptide chains of molecular weight approximately 23,000 daltons, and two identical heavy chains of molecular weight 53,000-70,000. The four chains are joined by disulfide bonds in a "Y" configuration. Heavy chains are classified as gamma (IgG), mu (IgM), alpha (IgA), delta (IgD) or epsilon (IgE) and are the basis for the class designations of immunoglobulins, which determines the effector function of a given antibody. Light chains are classified-as either kappa or lambda. When reference is made herein to an "immunoglobulin or fragment thereof", it will be understood that such a "fragment thereof" is an immunologically functional immunoglobulin fragment.

The term "humanized antibody" refers to an antibody molecule in which one or more amino acids of the antigen binding regions of a non-human antibody have been replaced in order to more closely resemble a human antibody, while retaining the binding activity of the original non-human antibody. See, e.g., U.S. Pat. No. 6,602,503.

The term "antigenic determinant", as used herein, refers to that fragment of a molecule (i.e., an epitope) that makes contact with a particular antibody. Numerous regions of a protein or fragment of a protein may induce the production of antibodies that binds specifically to a given region of the three-dimensional structure of the protein. These regions or structures are referred to as antigenic determinants. An antigenic determinant may compete with the intact antigen (i.e., the immunogen used to elicit the immune response) for binding to an antibody.

The term "fragment," when referring to a recombinant protein or polypeptide of the invention means a polypeptide which has an amino acid sequence which is the same as part of, but not all of, the amino acid sequence of the corresponding full length protein or polypeptide, and which retains at least one of the functions or activities of the corresponding full length protein or polypeptide. The fragment preferably includes at least 20-100 contiguous amino acid residues of the full-length protein or polypeptide.

A "multicistronic transcript" refers to an mRNA molecule that contains more than one protein coding region, or cistron. A mRNA comprising two coding regions is denoted a "bicistronic transcript." The "5'-proximal" coding region or cistron is the coding region whose translation initiation codon (usually AUG) is closest to the 5'-end of a multicistronic mRNA molecule. A "5'-distal" coding region or cistron is one whose translation initiation codon (usually AUG) is not the closest initiation codon to the 5' end of the mRNA. The terms "5'-distal" and "downstream" are used synonymously to refer to coding regions that are not adjacent to the 5' end of a mRNA molecule.

As used herein, "co-transcribed" means that two (or more) coding regions or polynucleotides are under transcriptional control of a single transcriptional control or regulatory element.

As used herein, an "internal ribosome entry site" or "IRES" refers to an element that promotes direct internal ribosome entry to the initiation codon, such as ATG, of a cistron (a protein encoding region), thereby leading to the cap-independent translation of the gene. Jackson R J, Howell M T, Kaminski A (1990) Trends Biochem Sci 15(12):477-83) and Jackson R J and Kaminski, A. (1995) RNA 1(10):985-1000). The present invention encompasses the use of any IRES element, which is able to promote direct internal ribosome entry to the initiation codon of a cistron. "Under translational control of an IRES" as used herein means that translation is associated with the IRES and proceeds in a cap-independent manner. Examples of "IRES" known in the art include, but are not limited to IRES obtainable from picornavirus (Jackson et al., 1990, Trends Biochem Sci 15(12): 477-483); and IRES obtainable from viral or cellular mRNA sources, such as for example, immunoglobulin heavy-chain binding protein (BiP), the vascular endothelial growth factor (VEGF) (Huez et al. (1998) Mol. Cell. Biol. 18(11):6178-6190), the fibroblast growth factor 2, and insulin-like growth factor, the translational initiation factor eIF4G, yeast transcription factors TFIID and HAP4. As used herein, "IRES" encompasses functional variations of IRES sequences as long as the variation is able to promote direct internal ribosome entry to the initiation codon of a cistron. In preferred embodiments, the IRES is mammalian. In other embodiments, the IRES is viral or protozoan. Examples of IRES sequences are described in U.S. Pat. No. 6,692,736.

The terms "coding sequence" and "coding region" refer to a nucleic acid sequence that is transcribed into RNA such as mRNA, rRNA, tRNA, snRNA, sense RNA or antisense RNA. In one embodiment, the RNA is then translated in a cell to produce a protein.

The term "inhibiting tumor growth" or "inhibition of tumor growth" refers to any measurable decrease in tumor mass, tumor volume, amount of tumor cells, or growth rate of the tumor. The definition is meant to include any diminution in the size, potency or growth rate of a pre-existing tumor. This includes suppression, regression, or partial or complete disappearance of a pre-existing tumor. Also, included in the definition is the inhibition or slowing of the increase in tumor size or tumor cell number, or the reduction in tumor cell number, tumor size, or numbers of tumors.

By the term "antigen from a tumor cell" or grammatical equivalents thereof, herein is meant any protein, carbohydrate or other component from a tumor cell capable of eliciting an immune response. The definition is meant to include, but is not limited to, using the whole tumor cell with all of its associated antigens as an antigen, as well as any component separated from the body of the cell, such as plasma membrane, cytoplasmic proteins, transmembrane proteins, proteins purified from the cell surface or membrane, or unique carbohydrate moieties associated with the cell surface. The definition also includes those antigens from the surface of the cell that require special treatment of the cells to access. Fragments of proteins that still contain immunological epitopes are included. One skilled in the art can determine immunogenic fragments of proteins as described herein.

The term "genetically modified tumor cell" as used herein refers to a composition comprising a population of cells that has been genetically modified to express a transgene, and that is administered to a patient as part of a cancer treatment regimen. The genetically modified tumor cell cancer immunotherapy comprises tumor cells which are "autologous" or "allogeneic" to the patient undergoing treatment or "bystander cells" that are mixed with tumor cells taken from the patient. A GM-CSF-expressing genetically modified tumor cell cancer immunotherapy is also referred to as "GVAX®".

By the term "systemic immune response" or grammatical equivalents herein is meant an immune response that is not localized, but affects the individual as a whole, thus allowing specific subsequent responses to the same stimulus.

The term "primary tumor cell" as used herein is a cancer cell that is isolated from a tumor in a mammal and has not been extensively cultured in vitro.

The term "enhanced expression" or "modified" to express as used herein, refers to a cell producing higher levels of a particular protein, peptide, mRNA or antigen (e.g. angiogenic protein, tumor antigen or cytokine) than would be produced in a naturally occurring cell or the parental cell from which it was derived. Cells may be genetically modified to increase the expression of an endogenous protein or mRNA using any methods known in the art, such as genetically modifying promoter regions of genomic sequences, genetically altering cellular signaling pathways to increase production of the protein or mRNA or by transduction with a vector coding for a protein, polypeptide or peptide of interest (e.g. a tumor antigen, angiogenic protein or cytokine). The term "cytokine" or "cytokines" as used herein refers to the general class of biological molecules, which affect cells of the immune system. The definition is meant to include, but is not limited to, those biological molecules that act locally or may circulate in the blood, and which, when used in the compositions or methods of the present invention serve to regulate or modulate an individual's immune response to cancer. Exemplary cytokines for use in practicing the invention include, but are not limited to, IFN-alpha, IFN-beta, and IFN-gamma, interleukins (e.g., IL-1 to IL-29, in particular, IL-2, IL-7, IL-12, IL-15 and IL-18), tumor necrosis factors (e.g., TNF-alpha and TNF-beta), erythropoietin (EPO), MIP3a, ICAM, macrophage colony stimulating factor (M-CSF), granulocyte colony stimulating factor (G-CSF) and granulocyte-macrophage colony stimulating factor (GM-CSF).

The term "increased immune response" as used herein means that a detectable increase of a specific immune activation is detectable (e.g. an increase in B-cell and/or T-cell response). An example of an increased immune response is an increase in the amount of an antibody that binds an antigen of a tumor cell. Another example is an increase of a cellular immune response. A cellular immune response involves T cells, and can be observed in vitro (e.g. measured by a Chromium release assay) or in vivo. An increased immune response is typically accompanied by an increase of a specific population of immune cells.

The term "administered" refers to any method that introduces the cells of the invention (e.g. cancer vaccine) to a mammal. This includes, but is not limited to oral, parenteral, intramuscular, subcutaneous, intradermal, intraperitoneal, intranasal, intravenous (including via an indwelling catheter), intratumoral, via an afferent lymph vessel, or by another route that is suitable in view of the tumor being treated and the mammal's condition. The compositions of this invention may be administered to the subject at any site. For example, they can be delivered to a site that is "distal" to or "distant" from the primary tumor.

The terms "treatment", "therapeutic use", or "medicinal use" as used herein, shall refer to any and all uses of the claimed compositions that remedy a disease state or symptoms, or otherwise prevent, hinder, retard, or reverse the progression of disease or other undesirable symptoms in any way whatsoever.

By the term "reversal of an established tumor" or grammatical equivalents herein is meant the suppression, regression, or partial or complete disappearance of a pre-existing tumor. The definition is meant to include any diminution in the size, potency or growth rate of a pre-existing tumor.

By the term "therapeutically effective amount" or grammatical equivalents herein refers to an amount of the preparation that is sufficient to modulate the systemic immune response of an individual or an amount sufficient to inhibit tumor growth. This amount may be different for different individuals, different tumor types, and different preparations. The "therapeutically effective amount" is determined using procedures routinely employed by those of skill in the art such that an "improved therapeutic outcome" results.

As used herein, the terms "improved therapeutic outcome" and "enhanced therapeutic efficacy", relative to cancer refers to a slowing or diminution of the growth of cancer cells or a solid tumor, or a reduction in the total number of cancer cells or total tumor burden. An "improved therapeutic outcome" or "enhanced therapeutic efficacy" therefore means there is an improvement in the condition of the individual according to any clinically acceptable criteria, including reversal of an established tumor, an increase in life expectancy or an improvement in quality of life.

By the term "individual", "subject", "mammalian subject" or grammatical equivalents thereof is meant any individual mammal.

Compositions and Methods of the Invention

The present invention provides cell-based cancer immunotherapy compositions that comprise a tumor antigen and one or both of an anti-CTLA4 antibody, and a cytokine. The cell-based cancer immunotherapy compositions of the invention are administered to a subject in order to stimulate an immune response to a tumor antigen (cancer) and/or to improve the therapeutic outcome for a cancer patient, following administration of the immunotherapy in vivo. In one embodiment, the cell-based tumor immunotherapy composition expresses a protein that will elicit an immune response to a tumor cell and an anti-CTLA4 antibody from a single cell. The subject is a mammal and typically a human cancer patient.

While the mechanism is not part of the invention, the efficacy of the cell-based cancer immunotherapy of the invention may be due to an enhanced immune response to one or more tumor antigens and/or blocking of the CTLA4-dependent inhibition of T-cell proliferation in the subject receiving the cancer immunotherapy.

Desirably, administration of the cell-based cancer immunotherapy of the invention effects a systemic immune response, i.e., a T-cell response and/or a B-cell response, to cancer. In one embodiment, the method comprises: genetically modifying a cell to express at least one of: a tumor antigen, an anti-CTLA4 antibody, and a cytokine; and administering the genetically modified cells to a subject, wherein the cells express at least one antigen expressed by the tumor cells harbored by cancer cells present in the subject to whom the cells are administered. The genetically modified cells may be tumor or cancer cells. The genetically modified cells are rendered proliferation incompetent prior to administration, typically by irradiation, although any known or later discovered method of rendering the cells proliferation incompetent may be employed. Upon administration of the genetically modified tumor cells to the subject, an enhanced immune response and/or the T-cell response to the cancer or tumor cells results.

The present invention is based on the observation that administration of a cytokine-expressing cancer immunotherapy comprised of tumor cells expressing GM-CSF that additionally locally expresses an anti-CTLA4 antibody exhibits prolonged survival in tumor-bearing animals compared to either as a monotherapy, and does so at significantly lower systemic levels of anti-CTLA4 antibody. (e.g., see Examples 5 and 6)

Genetically Modified Cytokine-Expressing Cells

In one aspect, the invention provides cell-based cancer immunotherapy composition that comprises a tumor antigen, an anti-CTLA4 antibody and a cytokine. The tumor antigen and cytokine are typically expressed by or from a cell. They may be expressed by the same cell or different cells, and one may be expressed by a cell while the other is provided in the form of the native protein or a biologically active fragment or variant thereof.

In one embodiment, a tumor cell is genetically modified to express a cytokine (e.g. GM-CSF) and an anti-CTLA4 antibody. The tumor cell is selected from the group consisting of an autologous tumor cell, an allogeneic tumor cell and a tumor cell line. The tumor cells may be transduced in vitro, ex vivo or in vivo. In practicing the present invention, the tumor cell may a primary tumor cell or a tumor cell line, typically of the same type as the tumor or cancer being treated. In general, human cells and cell line are used for administration to human patients.

Autologous and allogeneic cancer cells that have been genetically modified to express a cytokine, e.g., GM-CSF, followed by administration to an individual for the treatment of cancer are described in U.S. Pat. Nos. 5,637,483, 5,904,920 and 6,350,445. Clinical trials employing GM-CSF-expressing cancer immunotherapies (GVAX) have been undertaken for treatment of prostate cancer, melanoma, lung cancer, pancreatic cancer, renal cancer, and multiple myeloma. A number of clinical trials using these immunotherapies have been described, most notably in melanoma, and prostate, renal and pancreatic carcinoma (Simons J W et al. Cancer Res. 1999; 59:5160-5168; Simons J W et al. Cancer Res 1997; 57:1537-1546; Soiffer R et al. Proc. Natl. Acad. Sci USA 1998; 95:13141-13146; Jaffee, et al. J Clin Oncol 2001; 19:145-156; Salgia et al. J Clin Oncol 2003 21:624B30; Soiffer et al. J Clin Oncol 2003 21:3343B50; Nemunaitis et al. J Natl Cancer Inst. Feb. 18, 2004 96(4):326-31). A universal immunomodulatory genetically modified bystander cell line is described in U.S. Pat. No. 6,464,973, expressly incorporated by reference herein.

After transduction, the cells are irradiated to render them proliferation incompetent. The proliferation incompetent cytokine-expressing cells are then re-administered to the patient (e.g., by the intradermal or subcutaneous route) and thereby function as a cancer immunotherapy.

In one approach, the genetically modified tumor cells comprise a single population of cells that is modified to express a cytokine and an anti-CTLA4 antibody and is administered to a subject as part of a treatment regimen. In another approach, the same population or two or more populations of genetically modified tumor cells are modified to express a different transgene (e.g., a different cytokine or anti-CTLA4 antibody) and administered to a subject. The treatment regime may include one or more additional cancer therapeutic agents or treatments.

In general, the genetically modified tumor cells for use in practicing the invention include one or more of autologous tumor cells, allogeneic tumor cells, and tumor cell lines (i.e., bystander cells). A cell-based tumor immunotherapy of the invention may comprise any combination of cytokine-expressing autologous tumor cells, allogeneic tumor cells or bystander cells together with autologous tumor cells, allogeneic tumor cells or bystander cells that express a different cytokine and an anti-CTLA4 antibody.

The type of tumor being treated is selected from the group consisting of cancer of the bladder, breast, colon, head and neck cancer, kidney, liver, lung, ovary, cervix, pancreas, rectum, prostate, stomach, epidermis; a hematopoietic tumor of lymphoid or myeloid lineage; a tumor of mesenchymal origin such as a fibrosarcoma or rhabdomyosarcoma; other tumor types such as melanoma, teratocarcinoma, neuroblastoma, glioma, adenocarcinoma and non-small lung cell carcinoma. When the type of tumor cell being treated is prostate cancer, the prostate tumor cell line may be selected from the group consisting of DU145, PC-3, and LnCaP.

Autologous

The use of autologous cytokine-expressing tumor cells provides advantages since each patient's tumor expresses a unique set of tumor antigens that can differ from those found on histologically-similar, MHC-matched tumor cells from another patient. See, e.g., Kawakami et al., J. Immunol., 148, 638-643 (1992); Darrow et al., J. Immunol., 142, 3329-3335 (1989); and Hom et al., J. Immunother., 10, 153-164 (1991). In contrast, MHC-matched tumor cells from a different source provide the advantage that the patient need not be taken to surgery to obtain a sample of their tumor in order to prepare a cell-based cancer immunotherapy of the invention.

The use of autologous cytokine-expressing tumor cells provides advantages since each patient's tumor expresses a unique set of tumor antigens that can differ from those found on histologically-similar, MHC-matched tumor cells from another patient. See, e.g., Kawakami et al., J. Immunol., 148, 638-643 (1992); Darrow et al., J. Immunol., 142, 3329-3335 (1989); and Hom et al., J. Immunother., 10, 153-164 (1991). In contrast, MHC-matched tumor cells from a different source provide the advantage that the patient need not be taken to surgery to obtain a sample of their tumor in order to prepare a cell-based tumor vaccine of the invention In one preferred aspect, the present invention comprises a method of treating cancer by carrying out the steps of: (a) obtaining tumor cells from a mammalian subject harboring a tumor; (b) modifying the tumor cells to render them capable of expressing an anti-CTLA4 antibody and a cytokine; (c) rendering the modified tumor cells proliferation incompetent; and (d) readministering the modified tumor cells to the mammalian subject from which the tumor cells were obtained or to a mammal with the same MHC type as the mammal from which the tumor cells were obtained. The administered tumor cells are autologous and MHC-matched to the host. Preferably, the composition is administered subcutaneously, intradermally or intratumorally to the mammalian subject. A single autologous tumor cell may express the coding sequence for an anti-CTLA4 antibody and a cytokine or an anti-CTLA4 antibody and a cytokine may be expressed by different autologous tumor cells. In one aspect of the invention, an autologous tumor cell is modified by introduction of one or more vectors comprising a nucleic acid encoding an anti-CTLA4 antibody or a cytokine, e.g., GM-CSF, operatively linked to a promoter and expression/control sequences necessary for expression thereof. In another aspect, the same autologous tumor cell or a different autologous tumor cell is modified by introduction of a vector comprising a nucleic acid encoding an anti-CTLA4 antibody or a cytokine operatively linked to a promoter and expression/control sequences necessary for expression thereof. The nucleic acid encoding an anti-CTLA4 antibody or cytokine are introduced into the same or a different autologous tumor cell using the same or a different vector. Desirably, the autologous tumor cells express high levels of a cytokine, e.g., GM-CSF.

Allogeneic

Researchers have sought alternatives to autologous and MHC-matched cells as tumor vaccines, as reviewed by Jaffee et al., Seminars in Oncology, 22, 81-91 (1995). Early tumor immunotherapy strategies were based on the understanding that the vaccinating tumor cells function as the antigen presenting cells (APCs) that present tumor antigens on their MHC class I and II molecules, and directly activate the T cell arm of the immune system. The results of Huang et al. (Science, 264, 961-965, 1994), indicate that professional APCs of the host rather than the vaccinating tumor cells prime the T cell arm of the immune system by secreting cytokine(s) such as GM-CSF such that bone marrow-derived APCs are recruited to the region of the tumor. The bone marrow-derived APCs take up the whole cellular protein of the tumor for processing, and then present the antigenic peptide(s) on their MHC class I and II molecules, thereby priming both the CD4+ and the CD8+ T cell arms of the immune system, resulting in a systemic tumor-specific anti-tumor immune response. These results suggest that it may not be necessary or optimal to use autologous or MHC-matched tumor cells in order to elicit an anti-cancer immune response and that the transfer of allogeneic MHC genes (from a genetically dissimilar individual of the same species) can enhance tumor immunogenicity. More specifically, in certain cases, the rejection of tumors expressing allogeneic MHC class I molecules resulted in enhanced systemic immune responses against subsequent challenge with the unmodified parental tumor, as reviewed in Jaffee et al., supra, and Huang et al., supra.

As described herein, a "tumor cell line" comprises cells that were initially derived from a tumor. Such cells typically are transformed (i.e., exhibit indefinite growth in culture). In one preferred aspect, the invention provides a method for treating cancer by carrying out the steps of: (a) obtaining a tumor cell line; (b) modifying the tumor cell line to render the cells capable of expressing an anti-CTLA4 antibody and a cytokine; (c) rendering the modified tumor cell line proliferation incompetent; and (d) administering the tumor cell line to a mammalian subject (host) having at least one tumor that is of the same type of tumor as that from which the tumor cell line was obtained. The administered tumor cell line is allogeneic and is not MHC-matched to the host. Such allogeneic lines provide the advantage that they can be prepared in advance, characterized, aliquoted in vials containing known numbers of transgene-expressing cells and stored (i.e. frozen) such that well characterized cells are available for administration to the patient. Methods for the production of gene-modified allogeneic cells are described for example in WO 00/72686A1, expressly incorporated by reference herein.

In one approach to preparing genetically modified allogeneic cells, the coding sequence for more than one of a tumor antigen, an anti-CTLA4 antibody and a cytokine are introduced into a cell line that is an allogeneic tumor cell line (i.e., derived from an individual other than the individual being treated). In another approach, the coding sequence for more than one of a tumor antigen, an anti-CTLA4 antibody and a cytokine are introduced into separate allogeneic tumor cell lines. A tumor antigen may be expressed by the allogeneic cell line prior to genetic modification and/or a nucleic acid encoding a tumor antigen may be introduced into the allogeneic cell line by genetic modification. In general, the allogeneic cells are from a tumor cell line of the same type as the tumor or cancer being treated, examples of which are provided above.

In one aspect of the invention, an allogeneic tumor cell population is modified by introduction of one or more vectors comprising a nucleotide sequence encoding more than one of a tumor antigen, an anti-CTLA4 antibody or a cytokine, e.g., GM-CSF, operatively linked to a promoter and expression/control sequences necessary for expression thereof. In another aspect, a second cell population comprising an autologous, bystander or different allogeneic tumor cell population is modified by introduction of a vector comprising a nucleic acid sequence encoding a tumor antigen, an anti-CTLA4 antibody or a cytokine, e.g., GM-CSF, operatively linked to a promoter and expression/control sequences necessary for expression thereof. The nucleotide sequence encoding the tumor antigen, an anti-CTLA4 antibody or cytokine may be introduced into the same or a different autologous, allogeneic or bystander cell population using the same or a different vector. Desirably, the cells in the population express high levels of a cytokine, e.g., GM-CSF.

In practicing the invention, one or more genetically modified autologous, allogeneic or bystander cell lines may be incubated with the source of an autologous cancer antigen, e.g., an autologous tumor cell (which together comprise an allogeneic cell line composition), followed by administration to the patient. Typically, the cancer antigen is provided by (on) an autologous tumor cell of the same type as the cancer under treatment, i.e., an autologous cancer cell. In such cases, the composition is rendered proliferation-incompetent, typically by irradiation, wherein the genetically modified cells and cancer cells are plated in a tissue culture plate and irradiated at room temperature using a Cs source, as detailed below. The ratio of allogeneic cells to autologous cancer cells in a given administration will vary dependent upon the combination.

Any suitable route of administration can be used to introduce an allogeneic cell line composition into the patient, preferably, the composition is administered subcutaneously, intradermally or intratumorally.

The use of allogeneic cell lines in practicing present invention obviates the need to culture and transduce autologous tumor cells for each patient.

Bystander

In one further aspect, the present invention provides a universal immunomodulatory genetically modified bystander cell that expresses more than one of a tumor antigen, an anti-CTLA4 antibody and a cytokine. The same universal bystander cell line may express more than one of a tumor antigen, an anti-CTLA4 antibody and a cytokine or a tumor antigen, an anti-CTLA4 antibody and a cytokine may be expressed by different universal bystander cell lines. A tumor antigen may be expressed by the bystander cell line prior to genetic modification, and/or a nucleotide sequence encoding a tumor antigen may be introduced into the bystander cells by genetic modification. In general, the bystander cells express tumor antigens of the same type as the tumor or cancer being treated, examples of which are provided above.

The universal bystander cell line comprises cells which either naturally lack major histocompatibility class I (MHC-I) antigens and major histocompatibility class II (MHC-II) antigens or have been modified so that they lack MHC-I antigens and MHC-II antigens. In one aspect of the invention, a universal bystander cell line is modified by introduction of a vector comprising a nucleic acid sequence encoding more than one of: a tumor antigen, an anti-CTLA4 antibody and a cytokine, e.g., GM-CSF, operatively linked to a promoter and expression/control sequences necessary for expression thereof. In another aspect, a universal bystander cell line is modified by introduction of a vector comprising a nucleic acid sequence encoding at least one of: a tumor antigen, an anti-CTLA4 antibody and a cytokine, e.g., GM-CSF, operatively linked to a promoter and expression/control sequences necessary for expression and an allogeneic, autologous or second universal bystander cell line is modified by introduction of a vector comprising a nucleic acid sequence a tumor antigen, an anti-CTLA4 antibody or a cytokine, e.g., GM-CSF, operatively linked to a promoter and expression/control sequences necessary for expression thereof, then the two cell compositions are used together as a cellular vaccine. The nucleic acid sequence encoding the tumor antigen, an anti-CTLA4 antibody or cytokine may be introduced into the same or a different autologous, allogeneic or bystander cell population using the same or a different vector.

An example of a preferred universal bystander cell line is K562 (ATCC CCL-243; Lozzio et al., Blood 45(3): 321-334 (1975); Klein et al., Int. J. Cancer 18: 421-431 (1976)). A detailed description of the generation of human bystander cell lines is described for example in U.S. Pat. No. 6,464,973, expressly incorporated by reference herein.

Desirably, the universal bystander cell line expresses high levels of the cytokine, e.g., GM-CSF.

In practicing the invention, the one or more universal bystander cell lines may be incubated with an autologous cancer antigen, e.g., an autologous tumor cell (which together comprise a universal bystander cell line composition), then the universal bystander cell line composition is administered to the patient. Any suitable route of administration can be used to introduce a universal bystander cell line composition into the patient. Preferably, the composition is administered subcutaneously, intradermally or intratumorally.

Typically, the cancer antigen is provided by (on) a cell of the cancer to be treated, i.e., an autologous cancer cell. In such cases, the composition is rendered proliferation-incompetent by irradiation, wherein the bystander cells and cancer cells are plated in a tissue culture plate and irradiated at room temperature using a Cs source, as detailed above.

The ratio of bystander cells to autologous cancer cells in a given administration will vary dependent upon the combination. With respect to GM-CSF-producing bystander cells, the ratio of bystander cells to autologous cancer cells in a given administration should be such that a therapeutically effective level of GM-CSF is produced. In addition to the GM-CSF threshold, the ratio of bystander cells to autologous cancer cells should not be greater than 1:1. Appropriate ratios of bystander cells to tumor cells or tumor antigens can be determined using routine methods known in the art.

The use of bystander cell lines in practicing the present invention obviates the need to culture and transduce autologous tumor cells for each patient.

General Features of Cancer Immunotherapies of the Invention

The cell-based cancer immunotherapy of the invention may comprise one or more different cell populations, selected from unmodified tumor cells, tumor cells or non-tumor cells modified to express a cytokine and an anti-CTLA4 antibody, tumor cells or non-tumor cells modified to express an anti-CTLA4 antibody, tumor cells or non-tumor cells modified to express a cytokine, such as GM-CSF and the like. The cell-based cancer immunotherapies of the invention are rendered proliferation-incompetent prior to administration to a subject. As used herein, the term "proliferation-incompetent" or "inactivated" refers to cells that are unable to undergo multiple rounds of mitosis, but still retain the capability to express proteins such as cytokines, tumor antigens or angiogenic proteins. This may be achieved through numerous methods known to those skilled in the art. Prior to administration to a subject, the cell-based cancer immunotherapy of the invention are typically irradiated at a dose of from about 50 to about 200 rads/min or from about 120 to about 140 rads/min prior to administration to the subject. Typically, when using irradiation, the total levels required are 2,500 rads, 5,000 rads, 10,000 rads, 15,000 rads or 20,000 rads. Preferably, the cells are irradiated with a total dose sufficient to inhibit substantially 100% of the cells, from further proliferation.

The ratio of the number of cells modified to express an anti-CTLA4 antibody to the number of cells in a tumor antigen or cytokine-expressing cell population is between about 1:100 to 100:1, 25:1 to 1:25, 1:10 to 10:1, or 3:1 to 1:3. The different populations are delivered by the same route of administration and/or at about the same site and may be delivered at the same or at different times. In one embodiment of the invention, the immunotherapy comprises a mixture of allogeneic cells from a plurality of donors/individuals.

The genetically modified cells may be administered once twice or multiple times. For compositions comprising different populations of cells, typically between about $1 \times 10^6$ to $1 \times 10^9$ cells of each population are used. In one embodiment, there are between $1 \times 10^7$ and $1 \times 10^9$ cytokine producing cells per unit dose. In one embodiment, there are between $1 \times 10^8$ and $5 \times 10^8$. With multiple doses, the first immunization dose may be higher than subsequent immunization doses. For example, a $5 \times 10^8$ prime dose can be followed by several $1 \times 10^8$ to $3 \times 10^8$ booster doses of GM-CSF producing cells. In one aspect of the invention, the genetically modified cells of the immunotherapy are prepared and combined in bulk as to provide sufficient cells for the entire course of treatment envisioned. The mixture is stored frozen, and aliquots are thawed seriatim for each administration.

In one embodiment of the invention, the cancer immunotherapy comprises cells that express at least 500 ng or at least 36 ng of GM-CSF per 24 hours per one million cells. In one embodiment, the cancer immunotherapy comprises cells that express at least 1000 ng of GM-CSF per 24 hours per one million cells. Often more important than the actual number of cytokine-producing cells used is the biosynthetic capability of the cells, for example the amount of a cytokine, an anti-CTLA4 antibody or tumor antigen that is produced over time. Thus, fewer cells are required where the biosynthetic capability is higher. Embodiments of the invention include, but are not limited to, a dose of the immunotherapy that is capable of synthesizing at least about 0.1 ng, at about 0.5 ng, at least about 2 ng, or at least about 10 ng of the cytokine of interest during a 1 hour incubation under physiological conditions. Determination of optimal cell dosage and ratios is a matter of routine determination, as described in the examples section below, and within the skill of a practitioner of ordinary skill, in light of the instructions provided herein.

Typically following culture, the genetically modified cells of the invention are processed to remove most additional components used in preparing the cells prior to their use as a cancer immunotherapy. In particular, fetal calf serum, bovine serum components, or other biological supplements in the culture medium are removed. In one embodiment, the cells are washed, such as by repeated gentle centrifugation, into a suitable pharmacologically compatible excipient. Compatible excipients include isotonic saline, with or without a physiologically compatible buffer like phosphate or Hepes and nutrients such as dextrose, physiologically compatible ions, or amino acids, and various culture media, particularly those devoid of other immunogenic components. Carrying reagents, such as albumin and blood plasma fractions and nonactive thickening agents, may also be used. In one embodiment, non-active biological components, to the extent that they are present in the pharmacological preparation, are derived from a human, and may even be obtained previously from the subject to be treated.

The genetically modified cellular compositions of the invention can be used to treat cancer in a subject by administering them as one or more cancer immunotherapies. The pharmaceutical compositions of the present invention also may be administered in conjunction with an acceptable pharmaceutical carrier, such as, for example, saline solution, protamine sulfate (Elkins-Sinn, Inc., Cherry Hill, N.J.), water, aqueous buffers, such as phosphate buffers and Tris buffers, or Polybrene (Sigma Chemical, St. Louis, Mo.), or localizing agents such as calcitonin gel, hyaluronan solutions, or fibrin plugs derived from the activation of fibrinogen by thrombin (U.S. Pat. No. 6,117,425). The selection of a suitable pharmaceutical carrier is deemed to be apparent to those skilled in the art from the teachings contained herein.

The pharmaceutical compositions of this invention may be given following, preceding, in lieu of, or in combination with, other therapies relating to generating an immune response or treating cancer in the subject. For example, the subject may previously or concurrently be treated by chemotherapy, radiation therapy, and other forms of immunotherapy, using a treatment modality commonly used to treat the type of cancer under treatment using the cellular compositions of the present invention. For example, the compositions of the invention may be used in combination with such chemotherapeutic agents as Cisplatin, combination Cisplatin/Cyclophaphamide, Taxol or Cisplatin/Cyclophosphamide/Doxorobicin, immunomodulatory agents such as IL-2, IL-4, IL-7, IL-12, IL-15 IL-18, IL-21, INF alpha, CpG sequences, Iniquimod, or an anti-CTLA4 antibody. When such modalities are used, they are employed in a way or at a time that does not interfere with the efficacy of the compositions of the present invention.

Cytokines

The cell-based cancer immunotherapy may comprise the coding sequence for one or more cytokines. A "cytokine", includes, without limitation, those hormones that act locally and do not circulate in the blood, and which, when used in accordance with the present invention, will result in an alteration of an individual's immune response. Typically, the cytokine is a human cytokine.

Cytokines that may be expressed by the cell-based cancer immunotherapy of the invention include, but are not limited to, IFN-alpha, IFN-beta, and IFN-gamma, interleukins (e.g., IL-1 to IL-29, in particular, IL-2, IL-7, IL-12, IL-15 and IL-18), tumor necrosis factors (e.g., TNF-alpha and TNF-beta), erythropoietin (EPO), MIP3a, ICAM, macrophage colony stimulating factor (M-CSF), granulocyte colony stimulating factor (GCSF) and granulocyte-macrophage colony stimulating factor (GM-CSF). In one preferred embodiment, the cytokine is GM-CSF and the cell-based immunotherapy is a form of GVAX®.

Tumor Antigens

In cell-based cancer immunotherapy of the invention express at least one tumor antigen. The tumor antigen can be expressed by the autologous, allogeneic or bystander cell population prior to genetic modification or by expression of a native coding sequence from a vector coding for the tumor antigen(s). Tumor antigens of interest in practicing the invention are tumor antigens associated with the cancer under treatment and to which an enhanced immune response is desired. Exemplary cancer targets for treatment using the compositions and methods of the invention include but are not limited to cancer of the bladder, breast, colon, head and neck cancer, kidney, liver, lung, ovary, cervix, pancreas, rectum, prostate, stomach, epidermis; a hematopoietic tumor of lymphoid or myeloid lineage; a tumor of mesenchymal origin such as a fibrosarcoma or rhabdomyosarcoma; other tumor types such as melanoma, teratocarcinoma, neuroblastoma, glioma, adenocarcinoma and non-small lung cell carcinoma. When the type of tumor cell being treated is prostate cancer, the prostate tumor cell line may be selected from the group consisting of DU145, PC-3, and LnCaP.

Exemplary tumor antigen coding sequences include, but are not limited to, immunogenic sequences from MART-1, gp100 (pmel-17), tyrosinase, tyrosinase-related protein 1, tyrosinase-related protein 2, melanocyte-stimulating hormone receptor, MAGE1, MAGE2, MAGE3, MAGE12, BAGE, GAGE, NY-ESO-1, beta, catenin, MUM-1, CDK-4, caspase 8, KIA 0205, HLA-A2R1701, a-fetoprotein, telomerase catalytic protein, G-250, MUC-1, carcinoembryonic protein (CEA), p53, Her2/neu, triosephosphate isomerase, CDC-27, LDLR-FUT, telomerase reverse transcriptase, surviving, mesothelin, Ig-idiotype of B cell lymphoma, mutant cyclin dependent kinase 4 of melanoma, Pmel-17 (gp 100), PSMA, p15 protein of melanoma, gp75 of melanoma, oncofetal antigen of melanoma; GM2 and GD2 gangliosides of melanoma; oncogenes such as mutant p53 of carcinoma, mutant ras of colon cancer, and viral products such as human papilloma virus proteins of squamous cell cancers of cervix and esophagus.

In one embodiment, the tumor cell is derived from a mammal, such as a human, harboring a tumor.

Anti-CTLA4 Antibodies

CTLA4 (CD152) is an immunomodulatory molecule expressed by T-cells that through interactions with B7 molecules on antigen-presenting cells (APCs: B7-1 (CD80) and B7-2 (CD86)), negatively regulates T-cell activation in various model systems (e.g., see Korman et al. Curr. Opin. Invest. Drugs 6:582-591 (2005)). CTLA4 knockout mice exhibit massive lymphoproliferation leading to death in less than 4 weeks. Though CTLA4 has been studies extensively, its mechanism of action in reducing T-cell proliferation is not fully understood. It is believed that the mechanisms include B7 ligand competition at the APC and T-cell interface; signaling events that down regulate IL-2; induction of indoleamine 2,3-dioxygenase by APCs; and induction of negative regulatory cytokines.

Thus, an anti-CTLA4 antibody may have a therapeutic benefit as a monotherapy but systemic levels of anti-CTLA4 antibody necessary to observe efficacy in a clinical setting is near the maximum tolerated dose and has been reported to have related toxicity (e.g., see Korman et al. Curr. Opin. Invest. Drugs 6:582-591 (2005)). Therefore, there is a need to develop compositions that allow overcome the potential related toxicities by allowing for a lower systemic level of anti-CTLA4 antibody with equivalent efficacy.

Immunoglobulins and Fragments Thereof

Antibodies are immunoglobulin proteins that are heterodimers of a heavy and light chain and have proven difficult to express in a full length form from a single vector in mammalian culture expression systems. Three methods are currently used for production of vertebrate antibodies, in vivo immunization of animals to produce "polyclonal" antibodies, in vitro cell culture of B-cell hybridomas to produce monoclonal antibodies (Kohler, et al., Eur. J. Immunol., 6: 511, 1976; Antibodies: A Laboratory Manual, Cold Spring Harbor Laboratory, 1988; incorporated by reference herein) and recombinant DNA technology (described for example in Cabilly et al., U.S. Pat. No. 6,331,415, incorporated by reference herein).

The basic molecular structure of immunoglobulin polypeptides is well known to include two identical light chains with a molecular weight of approximately 23,000 daltons, and two identical heavy chains with a molecular weight 53,000-70,000, where the four chains are joined by disulfide bonds in a "Y" configuration. The amino acid sequence runs from the N-terminal end at the top of the Y to the C-terminal end at the bottom of each chain. At the N-terminal end is a variable region (of approximately 100 amino acids in length) which provides for the specificity of antigen binding.

The vectors allow for production of anti-CTLA4 immunoglobulins of all types, including, but not limited to full length antibodies and antibody fragments having a native sequence (i.e. that sequence produced in response to stimulation by an antigen), single chain antibodies which combine the antigen binding variable region of both the heavy and light chains in a single stably-folded polypeptide chain; univalent antibodies (which comprise a heavy chain/light chain dimer bound to the Fc region of a second heavy chain); "Fab fragments" which include the full "Y" region of the immunoglobulin molecule, i.e., the branches of the "Y", either the light chain or heavy chain alone, or portions, thereof (i.e., aggregates of one heavy and one light chain, commonly known as Fab'); "hybrid immunoglobulins" which have specificity for two or more different antigens (e.g., quadromas or bispecific antibodies as described for example in U.S. Pat. No. 6,623,940); "composite immunoglobulins" wherein the heavy and light chains mimic those from different species or specificities; and "chimeric antibodies" wherein portions of each of the amino acid sequences of the heavy and light chain are derived from more than one species (i.e., the variable region is derived from one source such as a murine antibody, while the constant region is derived from another, such as a human antibody).

The vectors find utility in production of anti-CTLA4 immunoglobulins or fragments thereof wherein the heavy or light chain is "mammalian", "chimeric" or modified in a manner to enhance its efficacy. Modified antibodies include both amino acid and nucleotide sequence variants which retain the same biological activity of the unmodified form and those which are modified such that the activity is altered, i.e., changes in the constant region that improve complement fixation, interaction with membranes, and other effector functions, or changes in the variable region that improve antigen binding characteristics. The compositions and methods of the invention further include catalytic immunoglobulins or fragments thereof.

A "variant" immunoglobulin-encoding polynucleotide sequence may encode a "variant" anti-CTLA4 immunoglobulin amino acid sequence which is altered by one or more amino acids from the reference polypeptide sequence. The variant polynucleotide sequence may encode a variant amino acid sequence which contains "conservative" substitutions, wherein the substituted amino acid has structural or chemical properties similar to the amino acid which it replaces. In addition, or alternatively, the variant polynucleotide sequence may encode a variant amino acid sequence which contains "non-conservative" substitutions, wherein the substituted amino acid has dissimilar structural or chemical properties to the amino acid which it replaces. Variant anti-CTLA4 immunoglobulin-encoding polynucleotides may also encode variant amino acid sequences which contain amino acid insertions or deletions, or both. Furthermore, a variant anti-CTLA4 immunoglobulin-encoding polynucleotide may encode the same polypeptide as the reference polynucleotide sequence but, due to the degeneracy of the genetic code, has a polynucleotide sequence which is altered by one or more bases from the reference polynucleotide sequence.

The term "fragment," when referring to a recombinant anti-CTLA4 immunoglobulin of the invention means a polypeptide which has an amino acid sequence which is the same as part of but not all of the amino acid sequence of the corresponding full length immunoglobulin protein, which either retains essentially the same biological function or activity as the corresponding full length protein, or retains at least one of the functions or activities of the corresponding full length protein. The fragment preferably includes at least 20-100 contiguous amino acid residues of the full-length immunoglobulin.

In preferred embodiments, an immunoglobulin expression system that permits the expression and delivery of two or more coding sequences, i.e., immunoglobulins with bi- or multiple-specificities from a single vector is employed. The immunoglobulin expression system is applicable to any anti-CTLA4 immunoglobulin (i.e. an antibody) or fragment thereof as further detailed herein, including engineered antibodies, e.g., single chain antibodies, full-length antibodies or antibody fragments.

The immunoglobulin expression system relies on the expression of anti-CTLA4 immunoglobulin heavy and light chains using a single regulated promoter wherein the heavy and light chains are expressed in substantially equal ratios. The linking of proteins in the form of polyproteins is a strategy adopted in the replication of many viruses including picornaviridae. Upon translation, virus-encoded self-processing peptides mediate rapid intramolecular (cis) cleavage of the polyprotein to yield discrete mature protein products and subsequent cleavage at the proteolytic cleavage site removes the majority of the remaining self-processing sequence. The immunoglobulin expression system provides advantages over the use of an IRES in that a vector for recombinant immunoglobulin expression comprising a self-processing peptide (exemplified herein by 2A peptides) is provided which facilitates expression of immunoglobulin heavy and light chain coding sequences using a single regulated promoter, wherein the immunoglobulin heavy and light chain coding sequences are expressed in a substantially equimolar ratio. The expression of the anti-CTLA4 heavy and light chains in substantially equal molar ratios may be demonstrated, for example, by Western blot analysis, where the heavy and light chain proteins are separated by SDS-PAGE under reducing conditions, probed using an anti-rat or anti-human IgG polyclonal antibody and visualized using commercially available kits according to the manufacturer's instructions.

Self-Processing Cleavage Sites or Sequences

A "self-processing cleavage site" or "self-processing cleavage sequence" as defined above refers to a DNA or amino acid sequence, wherein upon translation, rapid intramolecular (cis) cleavage of a polypeptide comprising the self-processing cleavage site occurs to yield discrete mature protein products. Such a "self-processing cleavage site", may also be referred to as a post-translational or co-translational processing cleavage site, exemplified herein by a 2A site, sequence or domain. A 2A site, sequence or domain demonstrates a translational effect by modifying the activity of the ribosome to promote hydrolysis of an ester linkage, thereby releasing the polypeptide from the translational complex in a manner that allows the synthesis of a discrete downstream translation product to proceed (Donnelly, 2001). Alternatively, a 2A site or domain demonstrates "auto-proteolysis" or "cleavage" by cleaving its own C-terminus in cis to produce primary cleavage products (Furler; Palmenberg, Ann. Rev. Microbiol. 44:603-623 (1990)).

The activity of 2A may involve ribosomal skipping between codons which prevents formation of peptide bonds (de Felipe et al., Human Gene Therapy 11:1921-1931 (2000); Donnelly et al., J. Gen. Virol. 82:1013-1025 (2001); although it has been considered that the domain acts more like an autolytic enzyme (Ryan et al., Virol. 173:35-45 (1989)). Studies in which the Foot and Mouth Disease Virus (FMDV) 2A coding region was cloned into expression vectors and transfected into target cells have established that FMDV 2A cleavage of artificial reporter polyproteins is efficient in a broad range of heterologous expression systems (wheat-germ lysate and transgenic tobacco plant (Halpin et al., U.S. Pat. No. 5,846,767 (1998) and Halpin et al., The Plant Journal 17:453-459 (1999)); Hs 683 human glioma cell line (de Felipe et al., Gene Therapy 6:198-208 (1999); hereinafter referred to as "de Felipe II"); rabbit reticulocyte lysate and human HTK-143 cells (Ryan et al., EMBO J. 13:928-933 (1994)); and insect cells (Roosien et al., J. Gen. Virol. 71:1703-1711 (1990)). FMDV 2A-mediated cleavage of a heterologous polyprotein has been shown for IL-12 (p40/p35 heterodimer; Chaplin et al., J. Interferon Cytokine Res. 19:235-241 (1999)). In transfected COS-7 cells, FMDV 2A mediated the cleavage of a p40-2A-p35 polyprotein into biologically functional subunits p40 and p35 having activities associated with IL-12.

The FMDV 2A sequence has been incorporated into retroviral vectors, alone or combined with different IRES sequences to construct bicistronic, tricistronic and tetracistronic vectors. The efficiency of 2A-mediated gene expression in animals was demonstrated by Furler (2001) using recombinant adeno-associated viral (AAV) vectors encoding a-synuclein and EGFP or Cu/Zn superoxide dismutase (SOD-1) and EGFP linked via the FMDV 2A sequence. EGFP and a-synuclein were expressed at substantially higher levels from vectors which included a 2A sequence relative to corresponding IRES-based vectors, while SOD-1 was expressed at comparable or slightly higher levels. Furler also demonstrated that the 2A sequence results in bicistronic gene expression in vivo after injection of 2A-containing AAV vectors into rat substantia nigra. Recently, 2A peptides and 2A-like sequences were demonstrated to be effective in efficient translation of four cistrons using a retroviral vector (Szymczak A L et al., Nat Biotechnol. May 22, 2004(5):589-94).

The DNA sequence encoding a self-processing cleavage site is exemplified by viral sequences derived from a picornavirus, including but not limited to an entero-, rhino-, cardio-, aphtho- or Foot-and-Mouth Disease Virus (FMDV). In a preferred embodiment, the self-processing cleavage site coding sequence is derived from a FMDV. Self-processing cleavage sites include but are not limited to 2A and 2A-like domains (Donnelly et al., J. Gen. Virol. 82:1027-1041 (2001), expressly incorporated by reference in its entirety.

FMDV 2A is a polyprotein region which functions in the FMDV genome to direct a single cleavage at its own C-terminus, thus functioning in cis. The FMDV 2A domain is typically reported to be about nineteen amino acids in length (LLNFDLLKLAGDVESNPGP; SEQ ID NO: 1); (TLNFDLLKLAGDVESNPGP; SEQ ID NO: 2; Ryan et al., J. Gen. Virol. 72:2727-2732 (1991)), however oligopeptides of as few as fourteen amino acid residues (LLKLAGDVESNPGP; SEQ ID NO: 3) have been shown to mediate cleavage at the 2A C-terminus in a fashion similar to its role in the native FMDV polyprotein processing.

Variations of the 2A sequence have been studied for their ability to mediate efficient processing of polyproteins (Donnelly M L et al. 2001). Homologues and variants of a 2A sequence are included within the scope of the invention and include but are not limited to the sequences presented in Table 1, below:

TABLE 1

Table of Exemplary 2A Sequences

| | |
|---|---|
| LLNFDLLKLAGDVESNPGP | (SEQ ID NO: 1) |
| TLNFDLLKLAGDVESNPGP; | (SEQ ID NO: 2) |
| LLKLAGDVESNPGP | (SEQ ID NO: 3) |
| NFDLLKLAGDVESNPGP | (SEQ ID NO: 4) |
| QLLNFDLLKLAGDVESNPGP | (SEQ ID NO: 5) |
| APVKQTLNFDLLKLAGDVESNPGP. | (SEQ ID NO: 6) |
| VTELLYRMKRAETYCPRPLLAIHPTEARHKQKIVAP VKQTLNFDLLKLAGDVESNPGP | (SEQ ID NO: 7) |
| LLAIHPTEARHKQKIVAPVKQTLNFDLLKLAGDVES NPGP | (SEQ ID NO: 8) |
| EARHKQKIVAPVKQTLNFDLLKLAGDVESNPGP | (SEQ ID NO: 9) |

The small size of the 2A coding sequence further enables its use in vectors with a limited packaging capacity for a coding sequence such as AAV. The utility of AAV vectors can be further expanded since the 2A sequence eliminates the need for dual promoters. The expression level of individual proteins, polypeptides or peptides from a promoter driving a single open reading frame comprising more than two coding sequences in conjunction with 2A are closer to equimolar as compared to the expression level achievable using IRES sequences or dual promoters. Elimination of dual promoters also reduces promoter interference that may result in reduced and/or impaired levels of expression for each coding sequence.

In one preferred embodiment, the FMDV 2A sequence included in a vector according to the invention encodes amino acid residues comprising LLNFDLLKLAGDVESNPGP (SEQ ID NO:1). Alternatively, a vector according to the invention may encode amino acid residues for other 2A-like regions as discussed in Donnelly et al., J. Gen. Virol. 82:1027-1041 (2001) and including but not limited to a 2A-like domain from picornavirus, insect virus, Type C rotavirus, trypanosome repeated sequences or the bacterium, Thermatoga maritima.

Removal of Self-Processing Peptide Sequences.

One concern associated with the use of self-processing peptides, such as 2A or 2A-like sequences is that the N terminus of the first anti-CTLA4 antibody chain contains amino acids derived from the self-processing peptide, i.e. 2A-derived amino acid residues. These amino acid residues are "foreign" to the host and may elicit an immune response when the recombinant protein is expressed or delivered in vivo (i.e., expressed from a viral or non-viral vector in the context of gene therapy or administered as an in vitro-produced recombinant protein). In addition, if not removed, 2A-derived amino acid residues may interfere with protein secretion in cytokine-expressing tumor cells and/or alter protein conformation, resulting in a less than optimal expression level and/or reduced biological activity of the anti-CTLA4 antibody. The immunoglobulin expression system includes gene expression constructs, engineered such that a proteolytic cleavage site is provided between a polypeptide coding sequence and the self processing cleavage site (i.e., a 2A-sequence) as a means for removal of remaining self processing cleavage site derived amino acid residues following cleavage.

Examples of proteolytic cleavage sites are furin cleavage sites with the consensus sequence RXK(R)R (SEQ ID NO:

10), which can be cleaved by endogenous subtilisin-like proteases, such as furin and other serine proteases within the protein secretion pathway. As shown in U.S. Ser. No. 10/831, 302, expressly incorporated by reference herein, the 2A residues at the N terminus of the first protein can be efficiently removed by introducing a furin cleavage site RAKR (SEQ ID NO:15) between the first protein and the 2A sequence. In addition, use of a plasmid containing a nucleotide sequence encoding a 2A sequence and a furin cleavage site adjacent to the 2A site was shown to result in a higher level of protein expression than a plasmid containing the 2A sequence alone. This improvement provides a further advantage in that when 2A residues are removed from the N-terminus of the protein, longer 2A- or 2A like sequences or other self-processing sequences can be used. Such longer self-processing sequences such as 2A- or 2A like sequences may facilitate better equimolar expression of two or more polypeptides by way of a single promoter.

It is advantageous to employ anti-CTLA4 antibodies or analogues thereof with fully human characteristics. These reagents avoid the undesired immune responses induced by antibodies or analogues originating from non-human species. To address possible host immune responses to amino acid residues derived from self-processing peptides, the coding sequence for a proteolytic cleavage site may be inserted (using standard methodology known in the art) between the coding sequence for the first protein and the coding sequence for the self-processing peptide so as to remove the self-processing peptide sequence from the expressed polypeptide, i.e. the antibody. This finds particular utility in therapeutic or diagnostic antibodies for use in vivo.

Any additional proteolytic cleavage site known in the art which can be expressed using recombinant DNA technology vectors may be employed in practicing the invention. Exemplary additional proteolytic cleavage sites which can be inserted between the anti-CTLA4 antibody heavy or light chain and a self processing cleavage sequence (such as a 2A sequence) include, but are not limited to a:

a). Furin cleavage site: RXK(R)R (SEQ ID. NO:10);
   b). Factor Xa cleavage site: IE(D)GR (SEQ ID. NO:12);
   c). Signal peptidase I cleavage site: e.g. LAGFATVAQA (SEQ ID. NO:13); and
   d). Thrombin cleavage site: LVPRGS (SEQ ID. NO:14).

The 2A peptide sequence provides a "cleavage" side that facilitates the generation of both chains of an anti-CTLA4 immunoglobulin during the translation process. In one aspect, the C-terminus of the anti-CTLA4 immunoglobulin heavy chain, contains approximately 13 amino acid residues which are derived from the 2A sequence itself. The number of residual amino acids is dependent upon the 2A sequence used. When a furin cleavage site sequence, e.g., RAKR (SEQ ID NO: 15), is inserted between the first protein and the 2A sequence, the 2A residues are removed from the C-terminus of the first protein. However, mass spectrum data indicates that the C-terminus of the antibody heavy chain expressed from the RAKR (SEQ ID NO: 15)-2A construct contains two additional amino acid residues, RA, derived from the furin cleavage site RAKR (SEQ ID NO: 15).

These residual amino acids may be removed using, for example carboxypeptidase. Furin cleavage occurs at the C-terminus of the cleavage site, which has the consensus sequence RXR(K)R (SEQ Ill. NO:16), where X is any amino acid. In one aspect, the invention provides a means for removal of the newly exposed basic amino acid residues R or K from the C-terminus of the protein by use of an enzyme selected from a group of enzymes called carboxypeptidases (CPs), which include carboxypeptidase D, E and H (CPD, CPE, CM). Since CPs are able to remove basic amino acid residues at the C-terminus of a protein, all amino acid resides derived from a furin cleavage site which contain exclusively basic amino acids R or K, such as RKKR (SEQ ID. NO:17), RKRR (SEQ ID. NO:18), RRKR (SEQ ID. NO:19), RRRR (SEQ ID. NO:20), etc, can be removed by a CP. Anti CTLA4 immunoglobulin expression constructs that contain a 2A sequence and a furin cleavage site and which have basic amino acid residues at the C terminus may be constructed to evaluate efficiency of cleavage and residue removal. An exemplary construct design is the following: H chain-furin (e.g., RKKR (SEQ ID NO: 17), RKRR (SEQ ID NO: 18), RRKR (SEQ ID NO: 19) or RRRR (SEQ ID NO: 20))-2A-L chain or L chain-furin (e.g., RKKR (SEQ ID NO: 17), RKRR (SEQ ID NO: 18), RRKR (SEQ ID NO: 19) or RRRR (SEQ ID NO: 20))-2A-H chain.

As will be apparent to those of skill in the art, there is a basic amino acid residue (K) at the C terminus of the immunoglobulin heavy (H) chain (rendering it subject to cleavage with carboxypeptidase), while the immunoglobulin light (L) chain, terminates with a non-basic amino acid C.

Sequence Variants

In one embodiment of the invention, the nucleotide sequences encoding a tumor antigen, an anti-CTLA4 antibody or cytokine is the native sequence for the native protein, a biologically active or immunogenic fragment thereof. In addition, the coding sequence may be "recoded". A gene that is "recoded" refers to a coding sequence that is altered in such a manner that the polypeptide encoded by a nucleic acid remains the same as in the unaltered sequence but the nucleic acid sequence encoding the polypeptide is changed. It is well known in the art that due to degeneracy of the genetic code, there exist multiple DNA and RNA codons that can encode the same amino acid translation product. Furthermore, it is also known that different organisms have different preferences for utilization of particular codons to synthesize an amino acid.

Also included within the scope of the invention are genetically modified cells comprising sequence variants which encode a biologically active or immunogenic form of a tumor antigen, an anti-CTLA4 antibody or cytokine.

As used herein, the term "sequence identity" means nucleic acid or amino acid sequence identity in two or more aligned sequences, when aligned using a sequence alignment program. The term "% homology" is used interchangeably herein with the term "% identity" herein and refers to the level of nucleic acid or amino acid sequence identity between two or more aligned sequences, when aligned using a sequence alignment program. For example, as used herein, 80% homology means the same thing as 80% sequence identity determined by a defined algorithm, and accordingly a homologue of a given sequence has greater than 80% sequence identity over a length of the given sequence.

Optimal alignment of sequences for comparison can be conducted, e.g., by the local homology algorithm of Smith & Waterman, Adv. Appl. Math. 2: 482 (1981), by the homology alignment algorithm of Needleman & Wunsch, J Mol. Biol. 48: 443 (1970), by the search for similarity method of Pearson & Lipman, Proc. Nat'l. Acad. Sci. USA 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), by the BLAST algorithm, Altschul et al., J Mol. Biol. 215: 403-410 (1990), with software that is publicly available through the National Center for Biotechnology Information, or by visual inspection (sec generally, Ausubel et al., infra). For purposes of the present invention, optimal alignment of sequences for comparison is most preferably conducted by the local homology algorithm of Smith & Waterman, Adv. Appl. Math. 2: 482 (1981). See, also, Altschul, S. F. et al., 1990 and Altschul, S. F. et al., 1997.

The terms "identical" or percent "identity" in the context of two or more nucleic acid or protein sequences, refer to two or more sequences or subsequences that are the same or have a specified percentage of amino acid residues or nucleotides that are the same, when compared and aligned for maximum correspondence, as measured using one of the sequence comparison algorithms described herein, e.g. the Smith-Waterman algorithm, or by visual inspection.

In accordance with the present invention, also encompassed are sequence variants which encode a tumor antigen, an anti-CTLA4 antibody or a cytokine that have 80, 85, 88, 89, 90, 91, 92, 93, 94, 95, 96, 97, 98, 99% or more sequence identity to the native sequence.

A nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature (Tm) of the nucleic acid binding complex or probe. For example, "maximum stringency" typically occurs at about Tm−5° C. (5° below the Tm of the probe); "high stringency" at about 5-100 below the Tm; "intermediate stringency" at about 10-20° below the Tm of the probe; and "low stringency" at about 20-25° below the Tm. Functionally, maximum stringency conditions may be used to identify sequences having strict identity or near-strict identity with the hybridization probe; while high stringency conditions are used to identify sequences having about 80% or more sequence identity with the probe.

Moderate and high stringency hybridization conditions are well known in the art (see, for example, Sambrook, et al, 1989, Chapters 9 and 11, and in Ausubel, F. M., et al., 1993. An example of high stringency conditions includes hybridization at about 42° C. in 50% formamide, 5×SSC, 5×Denhardt's solution, 0.5% SDS and 100 ug/ml denatured carrier DNA followed by washing two times in 2×SSC and 0.5% SDS at room temperature and two additional times in 0.1× SSC and 0.5% SDS at 42° C. As used herein nucleotide coding sequences for a tumor antigen, an anti-CTLA4 antibody or cytokine include sequence variants that encode a polypeptide with the same biological activity as the tumor antigen, anti-CTLA4 antibody or cytokine polypeptides described herein and hybridize under moderate to high stringency hybridization conditions are considered to be within the scope of the present invention.

As a result of the degeneracy of the genetic code, a number of coding sequences can be produced which encode the same tumor antigen, anti-CTLA4 antibody or cytokine polypeptide. For example, the triplet CGT encodes the amino acid arginine. Arginine is alternatively encoded by CGA, CGC, CGG, AGA, and AGG. Therefore it is appreciated that such substitutions in the coding region fall within the sequence variants that are covered by the present invention.

It is further appreciated that such sequence variants may or may not hybridize to the parent sequence under conditions of high stringency. This would be possible, for example, when the sequence variant includes a different codon for each of the amino acids encoded by the parent nucleotide. Such variants are, nonetheless, specifically contemplated and encompassed by the present invention.

Introduction of Transgenes into a Cell.

The coding sequence for a tumor antigen, anti-CTLA4 antibody or a cytokine may be introduced into a cell using any method effective to result in expression by the cell. Typically vectors comprising a coding sequence of interest are prepared using routine molecular biological techniques routinely employed by those of skill in the art.

The present invention contemplates the use of any available vector for introduction of the coding sequence for a tumor antigen, anti-CTLA4 antibody or cytokine into cells. Exemplary vectors include but are not limited to, viral and non viral vectors.

Viral vector particles may be utilized for the purpose of transferring DNA, RNA or other nucleic acids into cells either in vitro or in vivo. Numerous forms of viral and non-viral vectors are known in the art. Exemplary vectors that may be utilized for practicing the invention include, but are not limited to, e.g. derived from MoMLV, MSCV, SFFV, MPSV, SNV etc), including lentiviruses (e.g. derived from HIV-1, HIV-2, SIV, BIV, FIV etc.), vaccinia virus vectors, herpes virus vectors (e.g., HSV), baculoviral vectors, cytomegalovirus (CMV) vectors, papillomavirus vectors, simian virus (SV40) vectors, Sindbis vectors, Rous sarcoma virus vectors semliki forest virus vectors, phage vectors, Epstein Barr virus vectors, herpes virus vectors adenovirus (Ad) vectors including replication competent, replication deficient and gutless forms thereof, baculovirus vectors, adeno-associated viral (AAV) vectors and nonviral plasmid vectors.

The vectors and constructs for expression of a tumor antigen, anti-CTLA4 antibody or a cytokine may be introduced into cells using standard methodology. Methods for transfection, transduction or infection are well known by those of skill in the art. The term "transduction" refers to the delivery of a nucleic acid molecule into a recipient cell either in vivo or in vitro via infection, internalization, transfection or any other means. Transfection may be accomplished by a variety of means known in the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics, see Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. Gene 13:197, 1981. Such techniques can be used to introduce one or more exogenous DNA moieties, such as a plasmid vector and other nucleic acid molecules, into suitable host cells. The term refers to both stable and transient uptake of the genetic material.

Vectors utilized in practicing the invention may optionally code for a selectable marker, such as neo, DHFR, Gln synthetase or ADA, followed by selection in the presence of the appropriate drug and isolation of clones. More than one vector may be used to introduce the coding sequences for a tumor antigen, anti-CTLA4 antibody into a cell. The invention is not limited to any sequential order for transduction. In other words, more than one vector may be used essentially simultaneously or sequentially in any order to transduce the cells.

In the case where more than one coding sequence for a tumor antigen, anti-CTLA4 antibody or a cytokine is introduced into a cell using a single vector, the coding sequences may be under the control of separate promoters or may be operatively linked to the same promoter and under translational control of an IRES, 2A or 2A-like sequence, such as described in U.S. Ser. No. 04/12793 and U.S. Ser. No. 04/12807, expressly incorporated by reference herein.

AAV Vectors

Adeno associated virus (AAV) is a helper dependent human parvovirus. AAV vectors have significant potential as gene transfer vectors because of their non-pathogenic nature, excellent clinical safety profile and ability to direct significant amounts of transgene expression in vivo. Recombinant AAV vectors are characterized in that they are capable of directing the expression and the production of the selected transgenic products in targeted cells. Thus, the recombinant vectors comprise at least all of the sequences of AAV essential for encapsidation and the physical structures for infection of target cells. Infection of a cell with an AAV viral vector incorporated into a viral particle, typically leads to integration of the viral vector into the host cell genome. Therefore, AAV vectors provide the potential for long-term expression from the cell, and "daughter cells" that are a result of cell division.

Recombinant AAV (rAAV) virions for use in practicing the present invention may be produced using standard methodology, known to those of skill in the art and are constructed such that they include, as operatively linked components in the direction of transcription, control sequences including transcriptional initiation and termination sequences, and the coding sequence for a transgene. These components are bounded on the 5' and 3' end by functional AAV ITR sequences. By "functional AAV ITR sequences" is meant that the ITR sequences function as intended for the rescue, replication and packaging of the AAV virion. Hence, AAV ITRs for use in the vectors of the invention need not have a wild type nucleotide sequence, and may be altered by the insertion, deletion or substitution of nucleotides or the AAV ITRs may be derived from any of several AAV serotypes. An AAV vector is a vector derived from an adeno associated virus serotype, including without limitation, AAV 1, AAV 2, AAV 3, AAV 4, AAV 5, AAV 6, AAV 7, AAV 8, etc. In some embodiments, the AAV vectors have the wild type REP and CAP genes deleted in whole or part, but retain functional flanking ITR sequences.

Typically, an AAV expression vector is introduced into a producer cell, followed by introduction of an AAV helper construct, where the helper construct includes AAV coding regions capable of being expressed in the producer cell and which complement AAV helper functions absent in the AAV vector. The helper construct may be designed to down regulate the expression of the large REP proteins (Rep78 and Rep68), typically by mutating the start codon following p5 from ATG to ACG, as described in U.S. Pat. No. 6,548,286. This is followed by introduction of helper virus and/or additional vectors into the producer cell, wherein the helper virus and/or additional vectors provide accessory functions capable of supporting efficient rAAV virus production. The producer cells are then cultured to produce rAAV. These steps are carried out using standard methodology. Replication defective AAV virions encapsulating the recombinant AAV vectors of the instant invention are made by standard techniques known in the art using AAV packaging cells and packaging technology. Examples of these methods may be found, for example, in U.S. Pat. Nos. 5,436,146; 5,753,500, 6,040, 183, 6,093,570 and 6,548,286. Further compositions and methods for packaging are described in Wang et al. (US 2002/0168342) and include those techniques within the knowledge of those of skill in the art.

Approximately 40 serotypes of AAV are currently known, however, new serotypes and variants of existing serotypes are still being identified today and are considered within the scope of the present invention. See Gao et al (2002), PNAS 99(18):11854 6; Gao et al (2003), PNAS 100(10):6081 6; Bossis and Chiorini (2003), J. Virol. 77(12):6799 810). Different AAV serotypes are used to optimize transduction of particular target cells or to target specific cell types within a particular target tissue. Particular AAV serotypes may more efficiently target and/or replicate in target tissue or cells. A single self-complementary AAV vector can be used in practicing the invention in order to increase transduction efficiency and result in faster onset of transgene expression (McCarty et al., Gene Ther. Aug. 2001; 8(16): 1248 54).

Suitable host cells for producing rAAV virions include mammalian cells, insect cells, microorganisms and yeast. Host cells can also be packaging cells in which the AAV REP and CAP genes are stably maintained in the host cell or alternatively host cells can be producer cells in which the AAV vector genome is stably maintained. Exemplary packaging and producer cells are derived from 293, A549 or HeLa cells. AAV vectors are purified and formulated using standard techniques known in the art.

Retroviral Vectors

Retroviral vectors are a common tool for gene delivery (Miller, 1992, Nature 357: 455 460). Retroviral vectors including lentiviral vectors may be used in practicing the present invention. Retroviral vectors have been tested and found to be suitable delivery vehicles for the stable introduction of a variety of genes of interest into the genomic DNA of a broad range of target cells. The ability of retroviral vectors to deliver a transgene(s) into cells makes retroviral vectors well suited for transferring genes into cells. Further, retroviruses enter host cells by the binding of retroviral envelope glycoproteins to specific cell surface receptors on the host cells. Consequently, pseudotyped retroviral vectors in which the encoded native envelope protein is replaced by a heterologous envelope protein that has a different cellular specificity than the native envelope protein (e.g., binds to a different cell surface receptor as compared to the native envelope protein) may also find utility in practicing the present invention.

The present invention provides retroviral vectors that include e.g., retroviral transfer vectors comprising one or more transgene sequences and retroviral packaging vectors comprising one or more packaging elements. In particular, the present invention provides pseudotyped retroviral vectors encoding a heterologous or functionally modified envelope protein for producing pseudotyped retrovirus.

The core sequence of the retroviral vectors of the present invention may be readily derived from a wide variety of retroviruses, including for example, B, C, and D type retroviruses as well as spumaviruses and lentiviruses (see RNA Tumor Viruses, Second Edition, Cold Spring Harbor Laboratory, 1985). An example of a retrovirus suitable for use in the compositions and methods of the present invention includes, but is not limited to, lentivirus. Other retroviruses suitable for use in the compositions and methods of the present invention include, but are not limited to, Avian Leukosis Virus, Bovine Leukemia Virus, Murine Leukemia Virus, Mink Cell Focus Inducing Virus, Murine Sarcoma Virus, Reticuloendotheliosis virus and Rous Sarcoma Virus. Particularly preferred Murine Leukemia Viruses include 4070A and 1504A (Hartley and Rowe, J. Virol. 19:19 25, 1976), Abelson (ATCC No. VR 999), Friend (ATCC No. VR 245), Graffi, Gross (ATCC No. VR 590), Kirsten, Harvey Sarcoma Virus and Rauscher (ATCC No. VR 998), and Moloney Murine Leukemia Virus (ATCC No. VR 190). Such retroviruses may be readily obtained from depositories or collections such as the American Type Culture Collection ("ATCC"; Rockville, Md.), or isolated from known sources using commonly available techniques.

Preferably, a retroviral vector sequence of the present invention is derived from a lentivirus. A preferred lentivirus is a human immunodeficiency virus, e.g., type 1 or 2 (i.e., HIV 1 or HIV 2, wherein HIV 1 was formerly called lymphadenopathy associated virus 3 (HTLV III) and acquired immune deficiency syndrome (AIDS) related virus (ARV)), or another virus related to HIV 1 or HIV 2 that has been identified and associated with AIDS or AIDS like disease. Other lentivirus vectors that may be used in practicing the invention include, a sheep Visna/maedi virus, a feline immunodeficiency virus (FIV), a bovine lentivirus (e.g. BIV; WO200366810), simian immunodeficiency virus (SIV), an equine infectious anemia virus (EIAV), and a caprine arthritis encephalitis virus (CAEV).

The various genera and strains of retroviruses suitable for use in the compositions and methods are well known in the art (see, e.g., Fields Virology, Third Edition, edited by B. N. Fields et al., Lippincott Raven Publishers (1996), see e.g., Chapter 58, Retroviridae: The Viruses and Their Replication, Classification, pages 1768 1771, including Table 1).

Retroviral packaging systems for generating producer cells and producer cell lines that produce retroviruses, and methods of making such packaging systems are known. The retroviral packaging systems for use in generating cell lines comprise at least two packaging vectors: a first packaging vector which comprises a first nucleotide sequence comprising a gag, a pol, or gag and pol genes; and a second packaging vector which comprises a second nucleotide sequence comprising a heterologous or functionally modified envelope gene. In one embodiment, the retroviral elements are derived from a lentivirus, such as HIV. Preferably, the vectors lack a functional tat gene and/or functional accessory genes (vif, vpr, vpu, vpx, nef). In another embodiment, the system further comprises a third packaging vector that comprises a nucleotide sequence comprising a rev gene. The packaging system can be provided in the form of a packaging cell that contains the first, second, and, optionally, third nucleotide sequences.

A variety of retroviral systems, and those skilled in the art will appreciate the common elements shared across differing groups of retroviruses are applicable. The description herein uses lentiviral systems as a representative example. However, all retroviruses share the features of enveloped virions with surface projections and containing one molecule of linear, positive sense single stranded RNA, a genome consisting of a dimer, and the common proteins gag, pol and env.

In one embodiment, the lentiviral vector packaging systems provide separate packaging constructs for gag/pol and env, and typically employ a heterologous or functionally modified envelope protein (e.g. VSVG envelope). In a further embodiment, lentiviral vector systems have the accessory genes, vif, vpr, vpu and nef, deleted or inactivated. In a further embodiment, the lentiviral vector systems have the tat gene deleted or otherwise inactivated (e.g., via mutation). In another embodiment, the gag and pol coding sequence are "split" in to two separate coding sequences or open reading frames as known in the art. Typically the split gag and pol coding sequences are operatively linked to separate heterologous promoters and may be located on different nucleic acid molecules.

Compensation for the regulation of transcription normally provided by tat can be provided by the use of a strong constitutive promoter, such as the human cytomegalovirus immediate early (HCMV IE) enhancer/promoter. Other promoters/enhancers can be selected based on strength of constitutive promoter activity, specificity for target tissue (e.g., liver specific promoter), or other factors relating to desired control over expression, as is understood in the art. For example, in some embodiments, it is desirable to employ an inducible promoter such as tet to achieve controlled expression. The gene encoding rev is preferably provided on a separate expression construct, such that the lentiviral vector system will involve four constructs (e.g. plasmids): one each for gag/pol, rev, envelope and the transfer vector. Regardless of the generation of the packaging system employed, gag and pol can be provided on a single construct or on separate constructs.

Typically, the packaging vectors are included in a packaging cell, and are introduced into a cell via transfection, transduction or infection. Methods for transfection, transduction or infection are well known by those of skill in the art. A retroviral transfer vector of the present invention can be introduced into a packaging cell line, via transfection, transduction or infection, to generate a producer cell or cell line. The packaging vectors of the present invention can be introduced into human cells or cell lines by standard methods including, e.g., calcium phosphate transfection, lipofection or electroporation. In some embodiments, the packaging vectors are introduced into the cells together with a dominant selectable marker, such as neo, DHFR, Gln synthetase or ADA, followed by selection in the presence of the appropriate drug and isolation of clones. A selectable marker gene can be linked physically to genes encoded by the packaging vector or may be co-introduced (e.g. cotransfected) with the packaging vector.

Stable cell lines, wherein the packaging functions are configured to be expressed by a suitable packaging cell, are known. For example, see U.S. Pat. No. 5,686,279; and Ory et al., Proc. Natl. Acad. Sci. (1996) 93:11400 11406, which describe packaging cells. Further description of stable cell line production can be found in Dull et al., 1998, J. Virology 72(11):8463 8471; and in Zufferey et al., 1998, J. Virology 72(12):9873 9880.

The packaging vectors of interest may contain additional changes to the packaging functions to enhance lentiviral protein expression and to enhance safety. For example, all of the HIV sequences upstream of gag can be removed. Also, sequences downstream of envelope can be removed. Moreover, steps can be taken to modify the vector to enhance the splicing and translation of the RNA.

Optionally, a conditional packaging system is used, such as that described by Dull et al., 1998, J. Virology 72(11):8463 8471. Also preferred is the use of a self inactivating vector (SIN), which improves the biosafety of the vector by deletion of the HIV 1 long terminal repeat (LTR) as described, for example, by Zufferey et al., 1998, J. Virology 72(12):9873 9880. Inducible vectors can also be used, such as through a tet inducible LTR.

Adenoviral Vectors

Adenoviral vectors as disclosed herein may be utilized to express tumor antigens, GM-CSF, an anti-CTLA4 antibody or any combination thereof.

As used herein, the terms "adenovirus" and "adenoviral particle" are used to refer to any and all viruses that may be categorized as an adenovirus, including any adenovirus that infects a human or an animal, including all groups, subgroups, and serotypes. Thus, as used herein, "adenovirus" and "adenovirus particle" refer to the virus itself or derivatives thereof and cover all serotypes and subtypes and both naturally occurring and recombinant forms, except where indicated otherwise. Such adenoviruses may be wildtype or may be modified in various ways known in the art or as disclosed herein. Such modifications include modifications to the adenovirus genome that are packaged in the particle in order to make an infectious virus. Such modifications include deletions known in the art, such as deletions in one or more of the E1a, E1b, E2a, E2b, E3, or E4 coding regions. The terms also include replication-specific adenoviruses; that is, viruses that preferentially replicate in certain types of cells or tissues but to a lesser degree or not at all in other types. Such viruses are sometimes referred to as "cytolytic" or "cytopathic" viruses (or vectors), and, if they have such an effect on neoplastic cells, are referred to as "oncolytic" viruses. (or vectors).

The present invention contemplates the use of any and all adenoviral serotypes to construct adenoviral vectors and virus particles according to the present invention. Adenoviral stocks that can be employed according to the invention include any adenovirus serotype. Adenovirus serotypes 1 through 51 are currently available from American Type Culture Collection (ATCC, Manassas, Va.), and the invention includes any other serotype of adenovirus available from any source. The adenoviruses that can be employed according to the invention may be of human or non-human origin, such as bovine, porcine, canine, simian, avian. For instance, an adenovirus can be of subgroup A (e.g., serotypes 12, 18, 31), subgroup B (e.g., serotypes 3, 7,11,14,16,21,34,35,50), subgroup C (e.g., serotypes 1,2,5,6), subgroup D (e.g., serotypes 8, 9, 10, 13, 15, 17, 19,20,22-30, 32,33,36-39,42-47,49, 51), subgroup E (serotype 4), subgroup F (serotype 40,41), or any other adenoviral serotype. Numerous examples of human and animal adenoviruses are available in the American Type Culture Collection.

Adenoviral vectors are limited by the size of their genome (Bett et al, J Virol 67:5911-5921, 1993).

The adenoviral vectors of the invention include replication incompetent and replication competent vectors. A replication-incompetent vector does not replicate, or does so at very low levels, in the target cell. In one aspect, a replication incompetent vector has at least one coding region in E1a, E1b, E2a, E2b or E4 inactivated, usually by deleting or mutating, part or all of the coding region. Methods for propagating these vectors are well known in the art.

Exemplary adenoviral vectors include, but are not limited to, DNA, DNA encapsulated in an adenovirus coat, adenoviral DNA packaged in another viral or viral-like form (such as herpes simplex, and AAV), adenoviral DNA encapsulated in liposomes, adenoviral DNA complexed with polylysine, adenoviral DNA complexed with synthetic polycationic molecules, conjugated with transferrin, or complexed with compounds such as PEG to immunologically "mask" the antigenicity and/or increase half-life, or conjugated to a nonviral protein.

The adenoviral vector particle may also include further modifications to the fiber protein as described below. In one embodiment, the adenoviral vectors of the invention further comprise a targeting ligand included in a capsid protein of the particle. For examples of targeted adenoviruses, see for example, WO 00/67576, WO 99/39734, U.S. Pat. No. 6,683, 170, U.S. Pat. No. 6,555,368, U.S. Pat. No. 5,922,315, U.S. Pat. No. 5,543,328, U.S. Pat. No. 5,770,442 and U.S. Pat. No. 5,846,782.

In addition, the adenoviral vectors of the present invention may also contain modifications to other viral capsid proteins. Examples of these mutations include, but are not limited to those described in U.S. Pat. Nos. 5,731,190, 6,127,525, and 5,922,315. Other modified adenoviruses are described in U.S. Pat. Nos. 6,057,155, 5,543,328 and 5,756,086.

Standard systems for generating adenoviral vectors for expression of inserted sequences are known in the art and are available from commercial sources, for example the Adeno-X? expression system from Clontech (Palo Alto, Calif.) (Clontechniques (January 2000) p. 10-12), the Adenovator Adenoviral Vector System and AdEasy, both from Qbiogene (Carlsbad, Calif.).

Cell Lines

The tumor cell may be an established tumor cell line that is grown and maintained in vitro. Established tumor cell lines include, but are not limited to, PC-3 (ATCC#CRL-1435), Hela (ATCC#CCL-2), A549 (ATCC#CCL-185), LNCaP (ATCC#CRL-1740), H157 (ATCC#CRL-5802), K562 (ATCC# CCL-243), Panc 10.05 (ATCC #CRL-2547; (Jaffe et al, Human Gene Therapy 1998; 9:1951-1971; Jaffee et al, Cancer J Sci Am 1998; 4(3): 194-203), Panc 6.03, CG 8020, CG 2505, SK-BR-3 (ATCC# HTB-30; Fogh et al., 1977), T47D (ATCC# HTB-133; Keydar et al., 1979), 3SKBR3-7 (Emens et al. Hum Gene Ther. March 2004; 15(3):313-37), 2T47DV (Emens et al. 2004), MCF-7, BT-474, HCC-1937, or H1359 cells. In another embodiment, the cell lined engineered to enhance expression of an anti-CTLA4 antibody is a tumor cell isolated from a mammal and transduced with a vector that causes enhanced expression of the anti-CTLA4 antibody. Then the engineered tumor cell can be administered back to the same or a different mammal as part of a cancer immunotherapy. It is understood that the descendants of a cell may not be completely identical (either morphologically, genotypically, or phenotypically) to the parent cell. Furthermore, the cells can be either an unselected population of cells or specific clones of cells. For example the cells can be genetically modified or screened for high expression levels of the anti-CTLA4 antibody, cytokine, tumor antigen, or any combination thereof. In one embodiment of the invention, the cells are human cells. In one embodiment, they are prostate cells. In one embodiment, the cells are cryopreserved prior to administration to a subject. In one embodiment, the cells are proliferation-incompetent.

In one embodiment, the cells can be maintained in culture for a number of replications and genetically altered, if necessary. In one embodiment, the cell is a neoplastic cell, a malignantly transformed cell, or the progeny of such cells. Cells may be deliberately transformed into long-lived cell lines by any method, including, but not limited to, fusion with other cell lines, treatment with a chemical carcinogen, infection with a suitable virus such as Epstein-Barr virus or oncogenic virus, or transduced with a coding region that codes for a protein that allows continuous propagation (e.g. large T-antigen from SV40). In one embodiment, the cell will be the progeny of a primary prostate tumor that has been established in ex vivo culture.

A cell for use in practicing the invention may be a tumor cell that is genetically modified as detailed herein. Exemplary tumor cell types are selected from the group consisting of a head and neck cancer cell, a cell from pre-neoplastic lesion, a cancerous polyp cell, a leukemia cell, a bladder cell, a breast cell, a colon cell, kidney (renal) cell, liver cell, lung cell, ovary cell, cervix cell, pancreas cell, rectum cell, prostate cell, stomach cell, epidermis cell, a hematopoietic cell of lymphoid or myeloid lineage; a cell of mesenchymal origin, a melanoma cell, a teratocarcinoma cell, a neuroblastoma cell, a glioma cell, an adenocarcinoma cell and a non-small lung cancer cell.

UTILITY OF THE INVENTION

The invention provides cellular immunotherapy compositions and methods for inducing an immune response to tumor cells based on use of such vaccines. The cellular compositions comprise cells modified to express one or more of a tumor antigen, anti-CTLA4 antibody and a cytokine.

One embodiment of the invention is a cell based cancer immunotherapy that is modified to express of an anti-CTLA4 antibody using the 2A immunoglobulin expression system. Typically, the cells are of the same type as the tumor cells in the subject. For example, if a subject has prostate cancer then a cell derived from a prostate cell is engineered to express one or more transgenes as detailed hereinabove. In another example, if a subject has lung cancer then a cell derived from lung is engineered to express one or more transgenes as detailed hereinabove.

Another embodiment of the invention is a method of increasing an immune response to a tumor cell, a tumor antigen, a cell involved in angiogenesis or any combination. The increased immune response may be humoral, cellular (T-cells) or both humoral and cellular and is preferably systemic. Preferably, the systemic immune response to the tumor results in tumor regression or inhibition of the growth of the tumor, thereby resulting in an improved therapeutic outcome for the subject.

Methods of Evaluating Therapeutic Efficacy

Compositions of the invention can also be used to treat subjects who may or may not have a detectable tumor. The subject may have been previously diagnosed and treated or be at substantial risk of developing cancer, or may been previously treated with another mode of therapy. The prior therapy may have included (but is not restricted to) surgical resection, radiotherapy, traditional chemotherapy, and other modes of immunotherapy.

Suitable means of monitoring the tumor or disease state will vary depending on the tumor characteristics. Measurable decreases in tumor mass can be detected by numerous methods known to those skilled in the art. These include direct measurement of accessible tumors, counting of tumor cells (e.g. present in blood), measurements of tumor antigens (e.g. Prostate Specific Antigen (PSA), Alpha fetoprotein (AFP)) and various visualization techniques (e.g. MRI, CAT-scan and X-rays). The following are examples of decreases in the growth rate of a tumor: decrease of AFP levels in serum, decrease in tumor size and/or a reduction in rate at which a tumor's size or cell number is increasing. Decreases in the tumor growth rate can correlate with longer survival time for a mammal with cancer.

A general cellular immune response may be measured as the T cell proliferative activity in cells, particularly PBL sampled from the subject after immunotherapy administration. Inactivated tumor cells either from the treated mammal or from which the immunotherapy is base, or tumor cells of the same tumor type are used as stimulators. A non-specific mitogen such as PHA serves as a positive control; incubation with an unrelated stimulator cell serves as a negative control. After incubation of the PBMCs with the stimulators for an appropriate period (e.g. 5 days), [3H]-thymidine incorporation is measured. If desired, determination of the subset of T cells that is proliferating can be performed using flow cytometry. T cell cytotoxicity (CTL) can also be measured. In this test, a T-cell population from the subject is used as effectors in a standard 51Cr release assay. Tumor cells are radiolabeled as targets with about 200 microCi of Na251CrO4 for 60 minutes at 371 C, followed by washing. T cells and target cells (~1× 104/well) are then combined at various effector-to-target ratios in 96-well, U-bottom plates. The plates are centrifuged at 100×g for 5 minutes to initiate cell contact, and are incubated for 4-16 hours at 371 C. with 5% CO2. Release of 51Cr is determined in the supernatant, and compared with targets incubated in the absence of T cells (negative control) or with 0.1% TRITON™ X-100 (positive control). Other methods to measure increased immune responses include, but are not limited to, antibody based assays (ELISA, RIA, Western blot), antigen specific-cellular assays, proliferation assays, cytolytic cell assays, and in vivo delayed-type hypersensitivity testing with recombinant tumor-associated antigen or immunogenic fragments or peptides from the antigen. More methods to measure increased immune responses include assays currently used to measure T-cell responses include, but are not limited to, delayed-type hypersensitivity testing, flow cytometry using peptide major histocompatibility complex tetramers, lymphoproliferation assay, enzyme-linked immunosorbant assay, enzyme-linked immunospot assay, cytokine flow cytometry, direct cytotoxicity assay, measurement of cytokine mRNA by quantitative reverse transcriptase polymerase chain reaction, and limiting dilution analysis. See, e.g., Lyerly H K, Semin Oncol. June 2003; 30(3 Suppl 8):9-16.

The information obtained from these tests is useful in determining how the patient is responding following administration of the genetically modified cellular vaccines of the invention. The test results may be helpful in optimizing the treatment for an individual subject. Additional doses of a genetically modified cellular immunotherapy may be given as appropriate, typically on a monthly, semimonthly, or a weekly basis, until an improved therapeutic outcome is detected. Thereafter, and particularly when the immunological or clinical benefit appears to subside, additional booster or maintenance doses may be given as required.

EXAMPLES

The present invention is described by reference to the following examples, which are offered by way of illustration and are not intended to limit the invention in any manner. Standard techniques well known in the art or the techniques specifically described below are utilized. Those skilled in the art will recognize, or be able to ascertain, using no more than routine experimentation, many equivalents to the specific embodiments of the invention described specifically herein. Such equivalents are intended to be encompassed within the scope of the following claims.

Example 1

Vector Cloning and Production

A retroviral vector comprising the nucleotide sequence encoding full-length, heavy and light chains of a murine anti-CTLA-4 monoclonal antibody was generated using standard molecular biology techniques. Retroviral and lentiviral vectors transfer vectors were constructed that encoded the full length heavy and light chains of a mouse anti-CTLA-4 monoclonal antibody linked by a furin cleavage site and self processing 2A sequence. To clone the mouse anti-CTLA-4 DNA sequences, total RNA was isolated from a hydridoma cell line (designated 9D9) that encodes a mouse anti-mouse IgG2b anti-CTLA-4 antibody. Total RNA was purified from the cell line using a conventional RNA purification kit (Qiagen), and cDNA was synthesized with reverse transcriptase from the 9D9 cell total RNA. The variable and constant regions of the antibody heavy and light chains were cloned from the cDNA using the Polymerase Chain Reaction (PCR). The nucleotide sequences of the full length monoclonal antibody heavy and light chains were analyzed using an automatic sequencing system (Applied Biosystems) and consensus variable region sequences were obtained from the sequencing data derived from multiple independent PCR reactions.

The DNA fragments that encode the full-length antibody heavy chain, a furin cleavage site, the 2A sequence, and the full-length antibody light chain were linked together by PCR extension. Artificial oligonucleotides for FMDV 2A sequence were synthesized based on the 2A peptide sequence APVKQTLNFDLLKLAGDVESNPGP (SEQ ID NO: 6). During the PCR, an EcoR I site was added to the 5' prime end of the heavy chain and a Not I site to the 3' prime end of the light chain. Using these restriction enzyme sites, the fused heavy chain-furin-2A-light chain DNA fragment was cloned into retroviral and lentiviral transfer vector plasmids.

The retroviral transfer vector plasmid (rkat3F3) used for these studies has previously been described (Finer et al., Blood 83: 43-50 (1994)), and was subsequently modified to contain additional restriction enzyme sites flanking the extracellular domain of human CD4 (F3). Retroviral vectors were generated by transient transfection as previously described (Finer et al., Blood 83: 43-50 (1994); Dull et al., J Virol 72: 8463-8471(1998)).

The 3rd generation lentiviral vector system has previously been described (Dull et al., J. Virol. 72:8463-8471, 1998). Briefly, the transfer vector contains a 5' chimeric RSV/LTR promoter, cPPT (Zennou et al., Cell 101:173-185, 2000), CAG promoter (Miyazaki et al., Gene 79:269-277, 1989), and SIN LTR (Zufferey et al., J. Virol. 72:9873-9880, 1998). For these studies, the promoter driving the expression of the antibodies is comprised of a CMV enhancer, the chicken beta-actin promoter and splice donor, and the rabbit beta-globin splice acceptor (CAG). Vector production, concentration, p24 analysis, and titer assays were performed as previously described (Dull et al., J. Virol. 72:8463-8471, 1998). Briefly, vectors were prepared by transient transfection in a 10 cm dish with 6.5 ug of pMDLg/pRRE, 2.5 ug of pRSV-Rev, 3.5 ug of pMD2.VSVG-Env, and 10 ug of transfer vector.

Retroviral and lentiviral vector particles were harvested after 24 hours, pooled, passed through a 0.2 um cellulose acetate filter, and concentrated by ultracentrifugation for 2 hrs 20 min at 19,500 rpm (50,000 g) in a SW28 swinging bucket rotor. Pellets were resuspended in PBS containing 40 mg/ml lactose and stored in aliquots at −80° C. Detection of the gag p24 protein was evaluated using an Alliance HIV-1 p24 ELISA kit (Perkin Elmer).

Example 2

Constructing Various B16F10 and CT26 Immunotherapy Cell Lines

The murine melanoma B16F10 cell line is commercially available from American Type Culture Collection (e.g., ATCC Accession No. CRL-6475). The retrovirally-transduced GM-CSF-secreting B16.GM cell line has been previously described (Dranoff et al, Proc Natl Acad Sci USA 90: 3539-43 (1993)). This cell line generates 150 ng/$10^6$ cell/24 hours of mouse GM-CSF. Cells are maintained in Dulbecco's Minimum Essential Medium (DMEM; Hyclone) supplemented with 10% heat inactivated FBS (Hyclone), 2 mM L glutamine, and 1× penicillin/streptomycin (JRH) in a humidified incubator with 5% CO2 at 37° C.

The murine colon carcinoma CT26 cell line is also commercially available from American Type Culture Collection (e.g., ATCC Accession No. CRL-2638). The CT26.GM cell line was generated using the retroviral construct encoding GM-CSF that was used in the construction of the B16.GM (Dranoff et al, Proc Natl Acad Sci USA 90: 3539-43 (1993)). This cell line generates 80 ng/$10^6$ cells/24 hours of mouse GM-CSF. Cells are maintained in Dulbecco's Minimum Essential Medium (DMEM; Hyclone) supplemented with 10% heat inactivated FBS (Hyclone), 2 mM L glutamine, and 1× penicillin/streptomycin (JRH) in a humidified incubator with 5% CO2 at 37° C.

The parental B16.GM and CT26.GM cell lines are transduced with the anti-CTLA4 anti-body-encoding retroviral vector as previously described (Dull et al., J Virol 72: 8463-8471(1998)) using 100:1 of concentrated viral supernatant. The anti-CTLA4 antibody expressing cells are generated by a single round of transduction, and expression of the anti-CTLA4 protein is confirmed by ELISA using a commercially available anti-IgG kits according to manufacturer's instructions.

Example 3

Recombinant Anti-CTLA4 Antibody Produced from the Retroviral Transduced, Cytokine-Expressing Tumor Cells is Functional and Augments T-cell Expansion The following study in C57Bl/6 mice demonstrates that the recombinant anti-CTLA4 antibody produced from retroviral transduced, cytokine-expressing tumor cells is functional and augments T-cell expansion. On Day—2, 1-3×$10^6$ splenocytes from DO11.01 transgenic mice, which produces T cells specific for the $OVA_{323-339}$ peptide in the context of I-$A^d$ class II MHC, were adoptively transferred intravenously into recipient BALB/C mice. On Day 0, mice were injected with 500 ug of the surrogate antigen, ovalbumin, and on Day 0 and Day 1 were injected SC dorsal with 100 ug of the following purified antibodies: an IgG2b control (ISOTYPE); the anti-CTLA4 antibody expressed from the murine 9D9 hybridoma (Hybridoma); the anti-CTLA4 antibody expressed from B16F10 cells engineered to express GM-CSF and the anti-CTLA4 antibody produced by 9D9 hybridoma (2A-anti-CTLA4); or control vehicle (NAÏVE). On Day 4, mice were euthanized, the spleens and lymph nodes were harvested, and OVA-expressing T-cells were identified using the KJ126 monoclonal-specific antibody capable of detecting DO11.01 transgenic T-cells and evaluated by FACs analysis. Shown is the absolute number of ovalbumin-specific CD4 T cells in spleen.

Figures 3A, 3B:
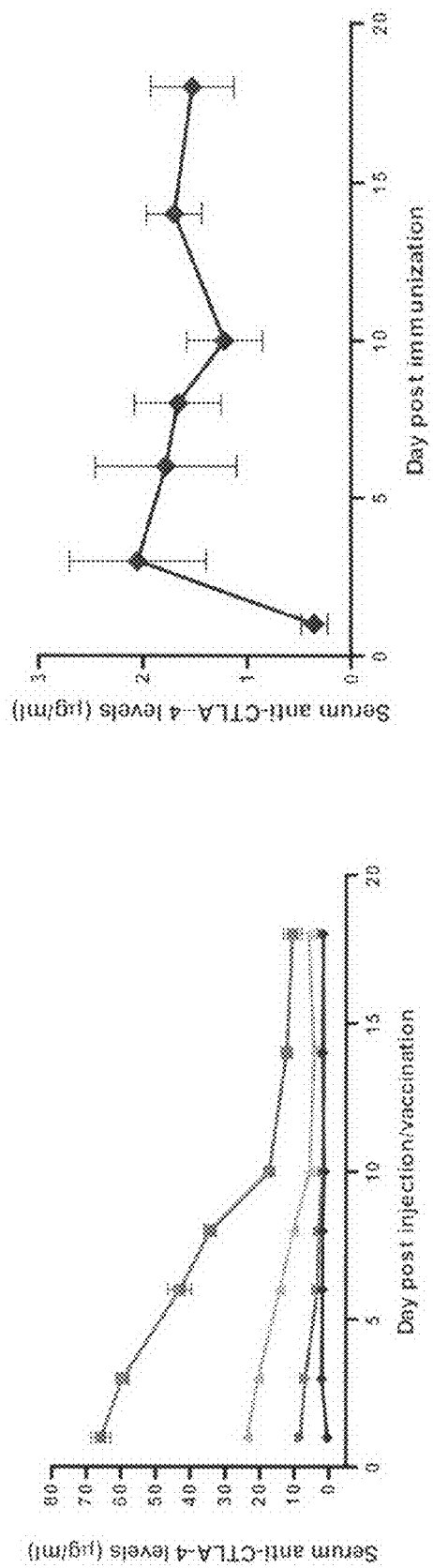
FIGS. 3A and B show of the results of a study in C57Bl/6 mice demonstrating that administration of a cytokine-expressing cancer immunotherapy that also locally expresses an anti-CTLA antibody results in long-term, sustainable, in vivo expression of anti-CTLA4 antibody. On Day 0, mice were inoculated subcutaneously (SC) with 2×10$^5$ live B16F10 tumor cells. On Day 1, mice were divided into 5 separate groups: one set each received a single intraperitoneal (ip) administration of 15 ug, 50 ug or 150 ug of purified anti-CTLA4 antibody, respectively; one set was immunized (SC) with 1×10$^6$ irradiated B16F10 tumor cells engineered to express GM-CSF; and the final set was immunized (SC) with 1×10$^6$ irradiated B16F10 tumor cells engineered to express GM-CSF and the anti-CTA4 antibody (FIG. 3B), and the serum levels of anti-CTLA4 antibody were followed for a period of 18 days.

As shown in FIG. 3, the anti-CTLA4 antibody expressed from the B16F10 tumor cells engineered to express GM-CSF and the anti-CTA4 antibody and that expressed by the parent hybridoma cell line augment T-cell expansion to essential same levels at essentially identical concentrations.

Example 4

Recombinant Anti-CTLA4 Antibody Produced In Vivo from Retroviral Transduced, Cytokine-Expressing Tumor Cells is Functional and Augments T-cell Expansion The following study in C57Bl/6 mice demonstrates that administration of a cytokine-expressing cancer immunotherapy that also locally expresses an anti-CTLA antibody results sustainable, systemic, in vivo expression of the anti-CTLA4 antibody. On Day 0, mice were inoculated subcutaneously (SC) with 2×$10^5$ live B16F10 tumor cells. On Day 1, mice were divided into 5 separate groups: one set each received a single intraperitoneal (ip) administration of 15 ug, 50 ug or 150 ug of purified anti-CTLA4 antibody, respectively; one set was immunized (SC) with 1×$10^6$ irradiated B16F10 tumor cells engineered to express GM-CSF; and the final set was immunized (SC) with 1×$10^6$ irradiated B16F10 tumor cells engineered to express GM-CSF and the anti-CTA4 antibody, and the serum levels of anti-CTLA4 antibody were followed for a period of 18 days.

As shown in FIG. 3, the anti-CTLA4 antibody expressed at the immunization site from the B16F10 tumor cells engineered to express GM-CSF and the anti-CTA4 antibody may be detected in serum at low, but sustainable levels for at least 18 days following a single administration of the cancer immunotherapy.

Example 5

Local Expression of an Anti-CTLA4 Antibody from Retroviral Transduced, Cytokine-expressing Tumor Cells Improves Survival of Tumor Bearing Animals at Lower systemic antibody concentrations. The following study in a BALB/c mouse CT26 tumor model demonstrates that retroviral transduced cytokine-expressing cancer immunotherapy expressing the anti-CTLA4 antibody improves survival of tumor bearing animals at lower systemic antibody concentrations. On Day 0, BALB/c mice were inoculated subcutaneously with $5 \times 10^5$ live CT26 tumor cells. Three days later, mice were immunized with $1 \times 10^6$ irradiated GM-CSF secreting CT-26, or with the same number of irradiated CT-26 cells secreting both GM-CSF and anti-CTLA4 antibody. Control groups were immunized on Day 3 with $1 \times 10^6$ irradiated GM-CSF secreting CT-26 tumor cells, and systemic (intraperitoneal—150 ug, 10 ug) or local SC (mixed with cytokine-expressing cancer immunotherapy—10 ug) administration of recombinant anti-CTLA4 antibody. Mice were monitored for the formation of palpable tumors twice weekly, and sacrificed if tumors became necrotic or exceeded 1500 mm³ in size.

The Kaplan Meier survival curve of surviving mice (n=10/group) is shown in FIG. 4A. In CT26 tumor-bearing mice, treatment with CT26 vaccine cells secreting GM-CSF only resulted in 20% survival on day 42, whereas 100% of the mice survived that were immunized with the CT26 tumor cells that secreted GM-CSF and anti-CTLA4 antibody locally at the immunization site. Serum from animals was collected at Day 3 post antibody administration and evaluated for anti-CTLA4 antibody levels using an ELISA assay (FIGS. 4B and 4C). Although 100% of animals treated with the GM-CSF secreting CT-26 tumor cell cancer immunotherapy plus systemic administration of the anti-CTLA4 antibody survived, anti-CTLA4 serum levels in this group were 7-fold higher than in the group that received the vaccine secreting the antibody locally. Furthermore, local delivery of the antibody from the secreting cells is more potent than local delivery of the recombinant antibody, which resulted in only 50% survival. These data show that local delivery of an anti-CTLA4 from antibody secreting cells improves cancer immunotherapy efficacy at lower systemic antibody exposure.

Example 6

Local Expression of an Anti-CTLA4 Antibody from Retroviral Transduced, Cytokine-Expressing Tumor Cells Improves Survival of Tumor Bearing Animals in B16F10 Melanoma Model To evaluate the local delivery of anti-CTLA4 in a different tumor model, B16F10 cells that secrete anti-CTLA4 antibody in addition to GM-CSF described above were examined. On Day 0, C57BL/6 mice were challenged with $2 \times 10^5$ live B16F10 tumor cells. Mice were immunized on Day 1 with $3 \times 10^6$ irradiated GM-CSF secreting B16F10 tumor cells, or with the same number of irradiated B16F10 cells secreting both GM-CSF and anti-CTLA4 antibody. A separate group was immunized with irradiated GM-CSF secreting tumor cells, and systemic (intraperitoneal) administration of recombinant antibody on Days 2 (150 ug) and 5 (100 ug). A second round of immunizations and antibody injections was administered starting on day 14. Tumor burden was monitored and mice were sacrificed when challenge tumors reached 1500 mm³ or severe ulceration developed.

The Kaplan Meier survival curve of surviving mice (n=10/group) from each group is shown in FIG. 5A. Whereas none of the mice treated with irradiated GM-CSF expressing cells only survived, 40% of the mice survived in the group treated with the anti-CTLA4 expressed locally from the cancer immunotherapy cells. 60% of the mice in the group immunized with GM-CSF secreting tumor cells and systemic anti-CTLA-4 antibody survived. Serum was collected at days 2, 3, 4, 7, 9, 11, 15, 16, 17, 23, and 25, and evaluated for anti-CTLA4 antibody levels using an ELISA assay (FIGS. 5B and 5c). These data show that the local delivery of anti-CTLA4 from cancer immunotherapy cells results in anti-tumor efficacy without exposing the host to high systemic antibody levels, thereby avoiding the associated anti-CTLA4 antibody toxicity reported at high systemic concentrations.

Example 7

Figure 6B:
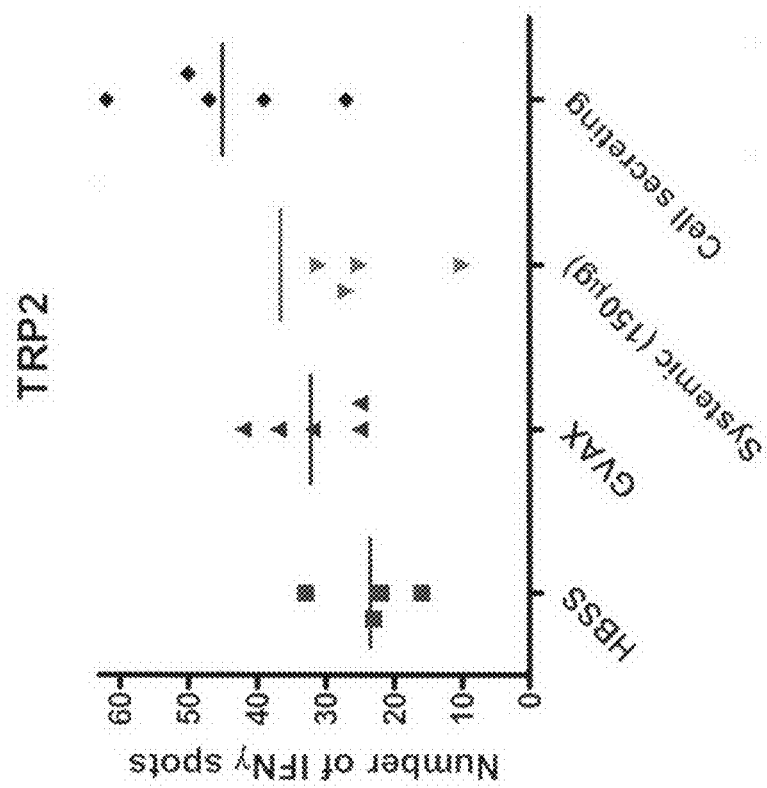
FIGS. 6A and 6B show the results of a study demonstrating that local expression of an anti-CTLA4 antibody from retroviral transduced, cytokine-expressing tumor cells results in enhanced T-cell responses. Satellite mice from the groups treated as described in FIG. 5 were collected at Day 21. Antigen specific responses were enumerated by an IFN-☐ ELISPOT assay (R&D Biosystems) according to the manufacturer's instructions. Erythrocyte-depleted splenocytes (5×10$^5$) were plated and incubated for 24 hr at 37° C., 5% CO2 with 1 uM of the Kb binding peptide derived from TRP2 (SVYDFFVWL) (SEQ ID NO: 11.
Figure 6A:
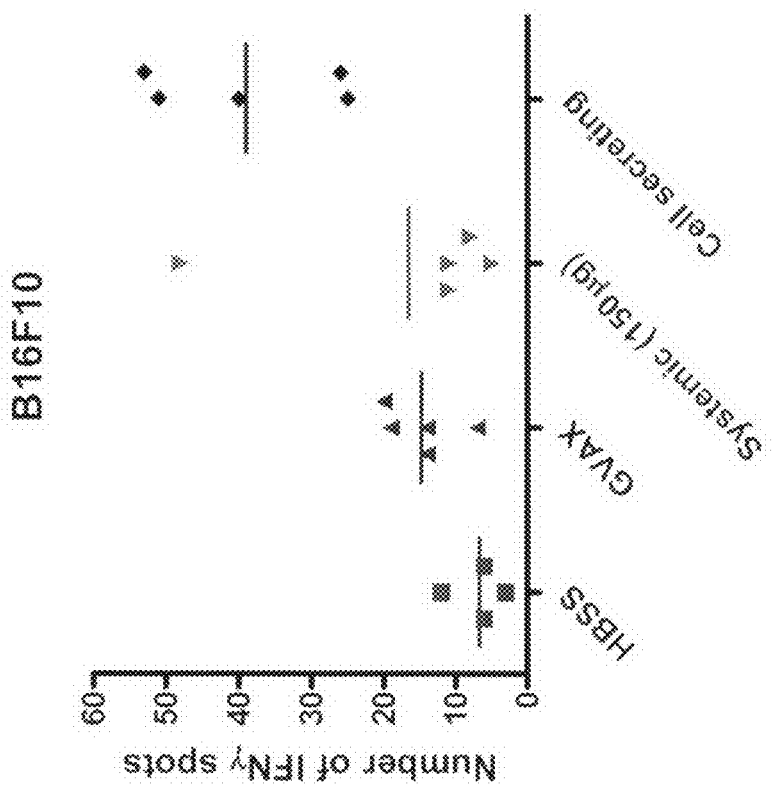

Local Expression of an Anti-CTLA4 Antibody from Retroviral Transduced, Cytokine-Expressing Tumor Cells Results in Enhanced T-cell Responses Satellite mice from the groups treated in Example 5 were collected at Day 21. Antigen specific responses were enumerated by an IFN-gamma ELISPOT assay (R&D Biosystems) according to the manufacturer's instructions. Erythrocyte-depleted splenocytes ($5 \times 10^5$) were plated and incubated for 24 hr at 37° C., 5% CO2 with 1 µM of the Kb binding peptide derived from TRP2 (SVYDFFVWL (SEQ ID NO: 11)) or $5 \times 10^3$ irradiated B16F10 cells. Positive spots were enumerated using an automated plate scanning service obtained from Cellular Technology Ltd. IFN-gamma ELISPOT assays using TRP2 and irradiated B16F10 stimulators revealed that the animals receiving the antibody secreting cells had increased numbers of activated T cells relative to animals treated with irradiated GM-CSF with or without systemic anti-CTLA4 administration (e.g., see FIGS. 6A and B).

Example 8

Local Expression of an Anti-CTLA4 Antibody using an F2A Casette Results in a Decreased Autoimmune Antibody Response The local delivery of anti-CTLA4 expressed using a 2A construct was evaluated in the B16F10 tumor model in C57Bl/6 mice. On Day 0, mice were inoculated subcutaneously (SC) with $2 \times 10^5$ live B16F10 tumor cells. On Day 1, mice were divided into 4 separate groups: one set each received a single intraperitoneal (ip) administration of HBSS; $3 \times 10^6$ irradiated B16F10 tumor cells engineered to express GM (B16GM); $3 \times 10^6$ irradiated B16GM plus a systemic injection of CTLA4 (B16GM systemic anti-CTLA4); or $3 \times 10^6$ irradiated B16GM engineered to secrete anti-CTLA-4 using an F2A cassette (B16GM F2A anti-CTLA4). This treatment regime was repeated bi-weekly. At various time points serum was collected and evaluated for the levels of anti-nuclear (FIG. 7A), ss-DNA (FIG. 7B), and ds-DNA (FIG. 7C) antibodies by ELISA. Decreased levels of autoimmune antibodies were observed in mice treated with F2A anti-CTLA-4 relative to mice treated with systemic (injected) anti-CTLA4.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

The invention claimed is:

1. A cellular composition for generating an immune response to cancer in a human subject, comprising: a tumor antigen and one or more populations of cells genetically modified to express the coding sequence for a granulocyte-macrophage colony stimulating factor (GM-CSF) polypeptide and the coding sequence of an anti-cytotoxic T lymphocyte-associated antigen-4 (CTLA-4) antibody, wherein the same population of cells is genetically modified to express the coding sequence for the GM-CSF polypeptide and the anti-CTLA-4 antibody.

2. The composition according to claim 1, wherein said tumor antigen is expressed by a cell.

3. The composition according to claim 1, wherein said genetically modified population of cells are tumor cells.

4. The composition according to claim 3, wherein said genetically modified population of tumor cells expresses said tumor antigen.

5. The composition according to claim 1, 3 or 4, wherein said anti-CTLA-4 antibody is expressed using a vector comprising:
in the 5' to 3' direction, a promoter operably linked to the coding sequence for the first chain of an anti-CTLA-4 antibody, a proteolytic cleavage site, a sequence encoding a self-processing cleavage site and the coding sequence for the second chain of an anti-CTLA-4 antibody, wherein the sequence encoding the self-processing cleavage site is inserted between the coding sequence for the first chain and the second chain of said anti-CTLA-4 antibody.

6. The composition according to claim 1, wherein said cells are autologous.

7. The composition according to claim 1, wherein said cells are allogeneic.

8. The composition according to claim 1, wherein said cells are bystander cells.

9. The composition according to claim 3, wherein said cells are autologous.

10. The composition according to claim 3, wherein said cells are allogeneic.

11. The composition according to claim 3, wherein said cells are bystander cells.

12. The composition according to claim 4, wherein said tumor antigen-expressing population of cells are autologous.

13. The composition according to claim 4, wherein said tumor antigen-expressing population of cells are allogeneic.

14. The composition according to claim 4, wherein said tumor antigen-expressing population of cells are bystander cells.

15. An improved method for cancer therapy
and generating an immune response to cancer to a human subject, by administering a cellular composition to a human subject, said composition comprising:
a tumor antigen and one or more populations of cells genetically modified to
express the coding sequence for a GM-CSF polypeptide and the coding sequence of an anti-cytotoxic T lymphocyte-associated antigen-4 (CTLA-4) antibody, wherein the same population of cells is genetically modified to express the coding sequence for the GM-CSF polypeptide and the anti-CTLA-4 antibody, and wherein administration of the composition to the subject results in an enhanced therapeutic efficacy relative to administration of a tumor antigen and a population of cells genetically modified to express the coding sequence for a GM-CSF polypeptide alone.

6. The method according to claim 15, wherein said tumor antigen is expressed by a cell.

17. The method according to claim 15, wherein said one or more populations of cells genetically modified to express the coding sequence for a GM-CSF polypeptide and the coding sequence of an anti-cytotoxic T lymphocyte-associated antigen-4 antibody are tumor cells.

18. The method according to claim 17, wherein said genetically modified population of tumor cells expresses said tumor antigen.

19. The method according to claim 15, wherein said anti-CTLA-4 antibody is expressed using a vector comprising:
in the 5' to 3' direction, a promoter operably linked to the coding sequence for the first chain of an anti-CTLA-4 antibody, a proteolytic cleavage site, a sequence encoding a self-processing cleavage site and the coding sequence for the second chain of an anti-CTLA-4 antibody, wherein the sequence encoding the self-processing cleavage site is inserted between the coding sequence for the first chain and the second chain of said anti-CTLA-4 antibody.

20. The method according to claim 15, wherein said cells genetically modified to express the coding sequence for a GM-CSF polypeptide and the coding sequence of an anti-cytotoxic T lymphocyte-associated antigen-4 antibody are autologous.

21. The method according to claim 15, wherein said cells genetically modified to express the coding sequence for a GM-CSF polypeptide and the coding sequence of an anti-cytotoxic T lymphocyte-associated antigen-4 antibody are allogeneic.

22. The method according to claim 15, wherein said cells genetically modified to express the coding sequence for a GM-CSF polypeptide and the coding sequence of an anti-cytotoxic T lymphocyte-associated antigen-4 antibody are bystander cells.

23. The method according to claim 17, wherein said cells genetically modified to express the coding sequence for a GM-CSF polypeptide and the coding sequence of an anti-cytotoxic T lymphocyte-associated antigen-4 antibody are autologous.

24. The method according to claim 17, wherein said cells genetically modified to express the coding sequence for a GM-CSF polypeptide and the coding sequence of an anti-cytotoxic T lymphocyte-associated antigen-4 antibody are allogeneic.

25. The method according to claim 17, wherein said cells genetically modified to express the coding sequence for a GM-CSF polypeptide and the coding sequence of an anti-cytotoxic T lymphocyte-associated antigen-4 antibody are bystander cells.

26. The method according to claim 18, wherein said cells genetically modified to express the coding sequence for a GM-CSF polypeptide and the coding sequence of an anti-cytotoxic T lymphocyte-associated antigen-4 antibody are autologous.

27. The method according to claim 18, wherein said cells genetically modified to express the coding sequence for a GM-CSF polypeptide and the coding sequence of an anti-cytotoxic T lymphocyte-associated antigen-4 antibody are allogeneic.

28. The method according to claim 18, wherein said cells genetically modified to express the coding sequence for a GM-CSF polypeptide and the coding sequence of an anti-cytotoxic T lymphocyte-associated antigen-4 antibody are bystander cells.

* * * * *

SEQUENCE LISTING

```
<160> NUMBER OF SEQ ID NOS: 20

<210> SEQ ID NO 1
<211> LENGTH: 19
<212> TYPE: PRT
<213> ORGANISM: Foot-and-mouth disease virus

<400> SEQUENCE: 1

Leu Leu Asn Phe Asp Leu Leu Lys Leu Ala Gly Asp Val Glu Ser Asn
1               5                   10                  15

Pro Gly Pro

<210> SEQ ID NO 2
<211> LENGTH: 19
<212> TYPE: PRT
<213> ORGANISM: Foot-and-mouth disease virus

<400> SEQUENCE: 2

Thr Leu Asn Phe Asp Leu Leu Lys Leu Ala Gly Asp Val Glu Ser Asn
1               5                   10                  15

Pro Gly Pro

<210> SEQ ID NO 3
<211> LENGTH: 14
<212> TYPE: PRT
<213> ORGANISM: Foot-and-mouth disease virus

<400> SEQUENCE: 3

Leu Leu Lys Leu Ala Gly Asp Val Glu Ser Asn Pro Gly Pro
1               5                   10

<210> SEQ ID NO 4
<211> LENGTH: 17
<212> TYPE: PRT
<213> ORGANISM: Foot-and-mouth disease virus

<400> SEQUENCE: 4

Asn Phe Asp Leu Leu Lys Leu Ala Gly Asp Val Glu Ser Asn Pro Gly
1               5                   10                  15

Pro

<210> SEQ ID NO 5
<211> LENGTH: 20
<212> TYPE: PRT
<213> ORGANISM: Foot-and-mouth disease virus

<400> SEQUENCE: 5

Gln Leu Leu Asn Phe Asp Leu Leu Lys Leu Ala Gly Asp Val Glu Ser
1               5                   10                  15

Asn Pro Gly Pro
            20

<210> SEQ ID NO 6
<211> LENGTH: 24
<212> TYPE: PRT
<213> ORGANISM: Foot-and-mouth disease virus
```

```
<400> SEQUENCE: 6

Ala Pro Val Lys Gln Thr Leu Asn Phe Asp Leu Leu Lys Leu Ala Gly
1               5                   10                  15

Asp Val Glu Ser Asn Pro Gly Pro
            20

<210> SEQ ID NO 7
<211> LENGTH: 58
<212> TYPE: PRT
<213> ORGANISM: Foot-and-mouth disease virus

<400> SEQUENCE: 7

Val Thr Glu Leu Leu Tyr Arg Met Lys Arg Ala Glu Thr Tyr Cys Pro
1               5                   10                  15

Arg Pro Leu Leu Ala Ile His Pro Thr Glu Ala Arg His Lys Gln Lys
            20                  25                  30

Ile Val Ala Pro Val Lys Gln Thr Leu Asn Phe Asp Leu Leu Lys Leu
        35                  40                  45

Ala Gly Asp Val Glu Ser Asn Pro Gly Pro
    50                  55

<210> SEQ ID NO 8
<211> LENGTH: 40
<212> TYPE: PRT
<213> ORGANISM: Foot-and-mouth disease virus

<400> SEQUENCE: 8

Leu Leu Ala Ile His Pro Thr Glu Ala Arg His Lys Gln Lys Ile Val
1               5                   10                  15

Ala Pro Val Lys Gln Thr Leu Asn Phe Asp Leu Leu Lys Leu Ala Gly
            20                  25                  30

Asp Val Glu Ser Asn Pro Gly Pro
        35                  40

<210> SEQ ID NO 9
<211> LENGTH: 33
<212> TYPE: PRT
<213> ORGANISM: Foot-and-mouth disease virus

<400> SEQUENCE: 9

Glu Ala Arg His Lys Gln Lys Ile Val Ala Pro Val Lys Gln Thr Leu
1               5                   10                  15

Asn Phe Asp Leu Leu Lys Leu Ala Gly Asp Val Glu Ser Asn Pro Gly
            20                  25                  30

Pro

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Lys or Arg

<400> SEQUENCE: 10
```

-continued

```
Arg Xaa Xaa Arg
1

<210> SEQ ID NO 11
<211> LENGTH: 9
<212> TYPE: PRT
<213> ORGANISM: Encephalomyocarditis virus

<400> SEQUENCE: 11

Ser Val Tyr Asp Phe Phe Val Trp Leu
1               5

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Glu or Asp

<400> SEQUENCE: 12

Ile Xaa Gly Arg
1

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Leu Ala Gly Phe Ala Thr Val Ala Gln Ala
1               5                   10

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Leu Val Pro Arg Gly Ser
1               5

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Ala Lys Arg
1

<210> SEQ ID NO 16
<211> LENGTH: 4
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Arg or Lys

<400> SEQUENCE: 16

Arg Xaa Xaa Arg
1

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Lys Lys Arg
1

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Arg Lys Arg Arg
1

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Arg Arg Lys Arg
1

<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Arg Arg Arg Arg
1
```